(12) United States Patent
Kurth et al.

(10) Patent No.: US 12,121,227 B2
(45) Date of Patent: *Oct. 22, 2024

(54) CARDIAC TRANSSEPTAL INSTRUMENTS, ASSEMBLIES, AND METHOD OF USE OF THE SAME

(71) Applicant: Pressure Products Medical Supplies Inc., Santa Barbara, CA (US)

(72) Inventors: Paul Kurth, Santa Barbara, CA (US); Andrew Armour, Swarthmore, PA (US); Reed Garrett, Wallingford, PA (US); William Gallo, Newtown Square, PA (US)

(73) Assignee: Pressure Products Medical Supplies, Inc., Santa Barbara, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 17/895,386

(22) Filed: Aug. 25, 2022

(65) Prior Publication Data
US 2022/0401090 A1    Dec. 22, 2022

Related U.S. Application Data

(62) Division of application No. 16/748,610, filed on Jan. 21, 2020, now Pat. No. 11,457,903.

(51) Int. Cl.
*A61B 17/00*    (2006.01)
*A61B 17/34*    (2006.01)

(52) U.S. Cl.
CPC .... *A61B 17/00234* (2013.01); *A61B 17/3478* (2013.01); *A61B 2017/00247* (2013.01); *A61B 2017/00867* (2013.01)

(58) Field of Classification Search
CPC .............. A61B 17/00234; A61B 17/34; A61B 17/3401; A61B 17/3417; A61B 17/3474; A61B 17/3478; A61B 17/3496; A61B 2010/045; A61B 2017/00243; A61B 2017/00247; A61B 2017/3454
See application file for complete search history.

(56) References Cited

U.S. PATENT DOCUMENTS

| | | | | |
|---|---|---|---|---|
| 5,836,914 | A * | 11/1998 | Houghton | A61B 17/3401 604/117 |
| 6,902,547 | B2 * | 6/2005 | Aves | A61N 1/0551 606/108 |
| 7,386,341 | B2 * | 6/2008 | Hafer | A61B 18/1492 607/3 |

(Continued)

*Primary Examiner* — Ryan J. Severson
(74) *Attorney, Agent, or Firm* — Marcus C. Dawes

(57) ABSTRACT

A needle or stylet has a tip contour with a reverse back bevel curved toward the longitudinal axis of the needle or stylet. The needle has a flexible intermediate portion and/or a two-part construction in which a distal portion of the needle to crimped onto a proximal portion of the needle. The needle or a stylet is combined with a spring mechanism in the hub of the needle or stylet assembly. The spring mechanism positions the tip of the needle or stylet in a middle position extending from the distal end of the assembly, allows the needle or stylet to be moved into a spring loaded fully retracted configuration within the assembly as the septal wall is tented, and then releasing the spring loaded needle or stylet as the needle or stylet penetrates the septal wall. A method of using a needle or stylet with a spring mechanism is included.

20 Claims, 22 Drawing Sheets

(56) References Cited

U.S. PATENT DOCUMENTS

| | | | |
|---|---|---|---|
| 7,635,353 B2* | 12/2009 | Gurusamy | A61M 25/065 604/170.03 |
| 7,666,203 B2 | 2/2010 | Chanduszko | |
| 8,114,110 B2* | 2/2012 | Bednarek | A61B 17/00234 604/272 |
| 8,157,829 B2* | 4/2012 | Chanduszko | A61B 17/0057 128/898 |
| 8,282,565 B2* | 10/2012 | Mahapatra | A61B 17/3401 604/246 |
| 8,292,910 B2* | 10/2012 | Chanduszko | A61B 17/0057 606/213 |
| 8,491,619 B2* | 7/2013 | Breznock | A61B 17/34 606/184 |
| 8,647,257 B2* | 2/2014 | Jansen | A61B 17/320016 600/114 |
| 8,992,556 B2* | 3/2015 | Chanduszko | A61B 17/0057 606/185 |
| 9,821,145 B2* | 11/2017 | Kurth | A61B 17/0057 |
| 10,485,569 B2* | 11/2019 | Lenker | A61B 17/3417 |
| 10,716,920 B2* | 7/2020 | Kurth | A61M 25/09041 |
| 10,729,457 B2* | 8/2020 | Lenker | A61B 90/39 |
| 11,090,080 B2* | 8/2021 | Lenker | A61M 29/00 |
| 11,457,903 B2* | 10/2022 | Kurth | A61B 17/3478 |
| 2003/0028147 A1* | 2/2003 | Aves | A61N 1/0551 604/272 |
| 2006/0064062 A1 | 3/2006 | Gurusamy | |
| 2007/0270741 A1* | 11/2007 | Hassett | A61M 25/0606 604/96.01 |
| 2012/0179188 A1* | 7/2012 | Chanduszko | A61B 17/0057 606/185 |
| 2015/0265777 A1 | 9/2015 | Whitley | |
| 2016/0175003 A1* | 6/2016 | Kafiluddi | A61B 17/3401 604/158 |
| 2017/0252520 A1* | 9/2017 | Higaki | A61B 17/3417 |
| 2018/0289388 A1 | 10/2018 | Lenker | |
| 2019/0038876 A1 | 2/2019 | Isaacson | |
| 2020/0113597 A1* | 4/2020 | Jenkins | A61B 17/3496 |
| 2020/0367924 A1* | 11/2020 | Lenker | A61B 17/32053 |
| 2021/0128122 A1* | 5/2021 | Stoianovici | A61B 10/0275 |
| 2021/0219968 A1* | 7/2021 | Kurth | A61B 17/3478 |
| 2021/0369296 A1* | 12/2021 | Lenker | A61M 29/00 |
| 2022/0401090 A1* | 12/2022 | Kurth | A61B 17/3478 |

* cited by examiner

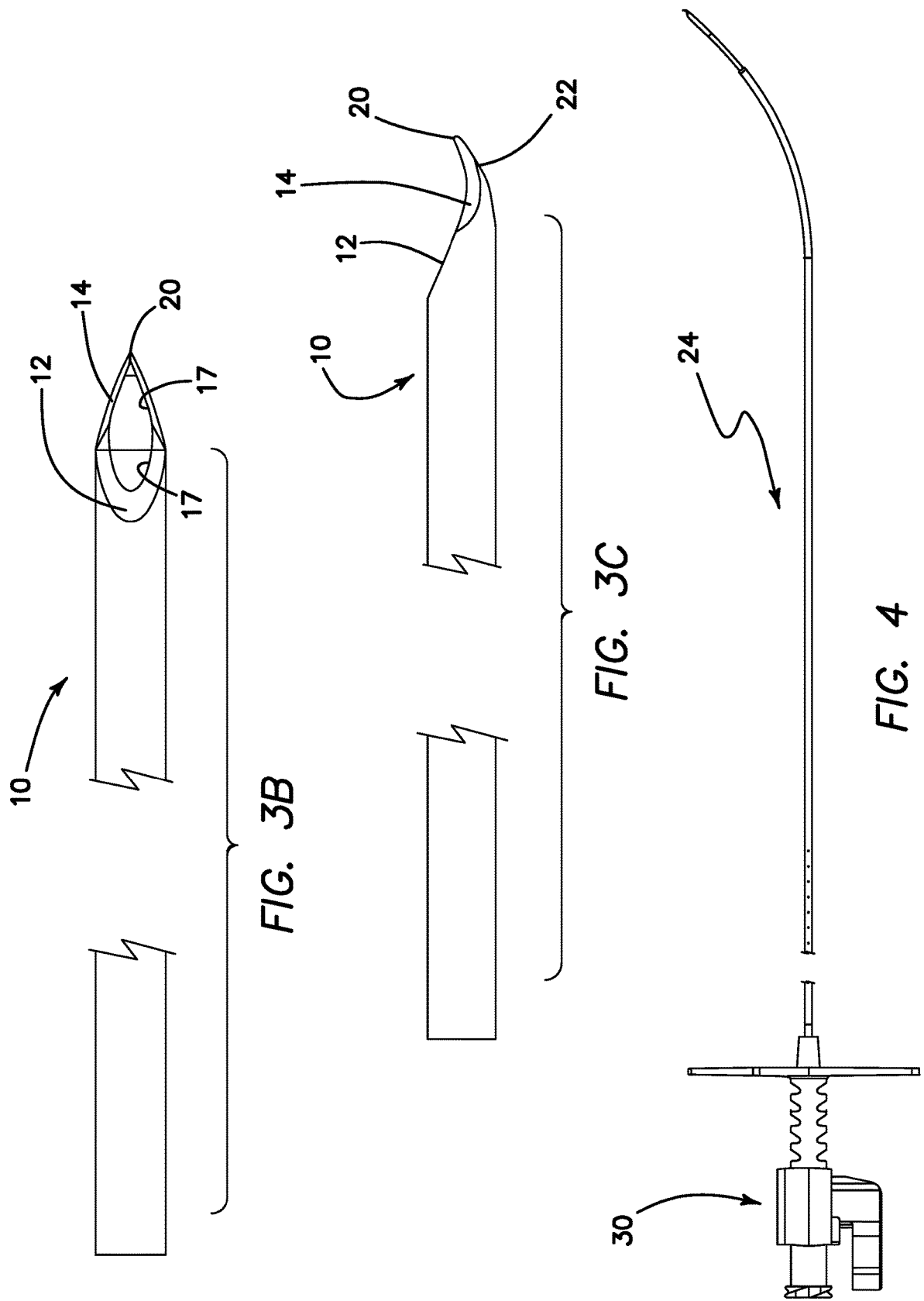

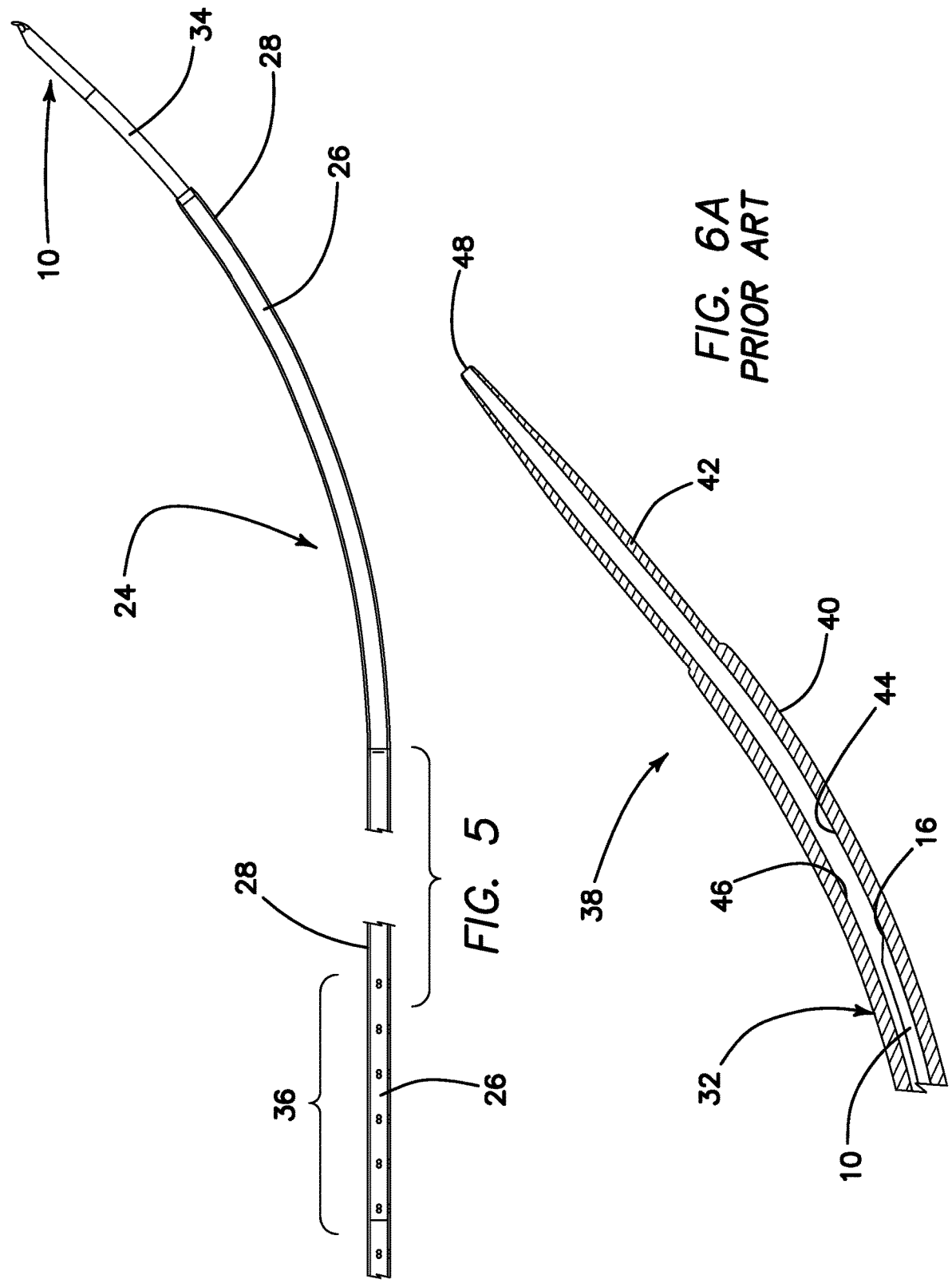

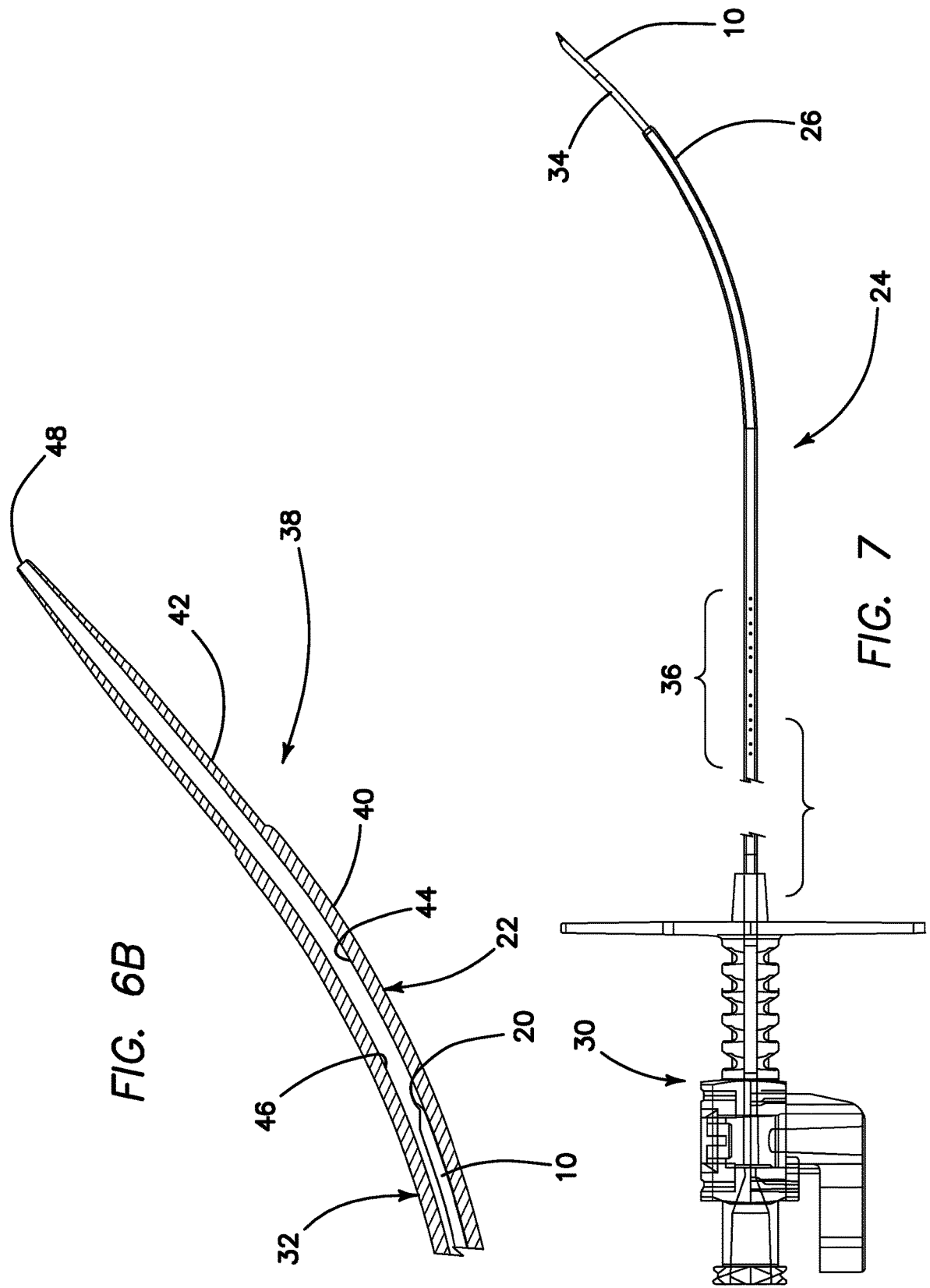

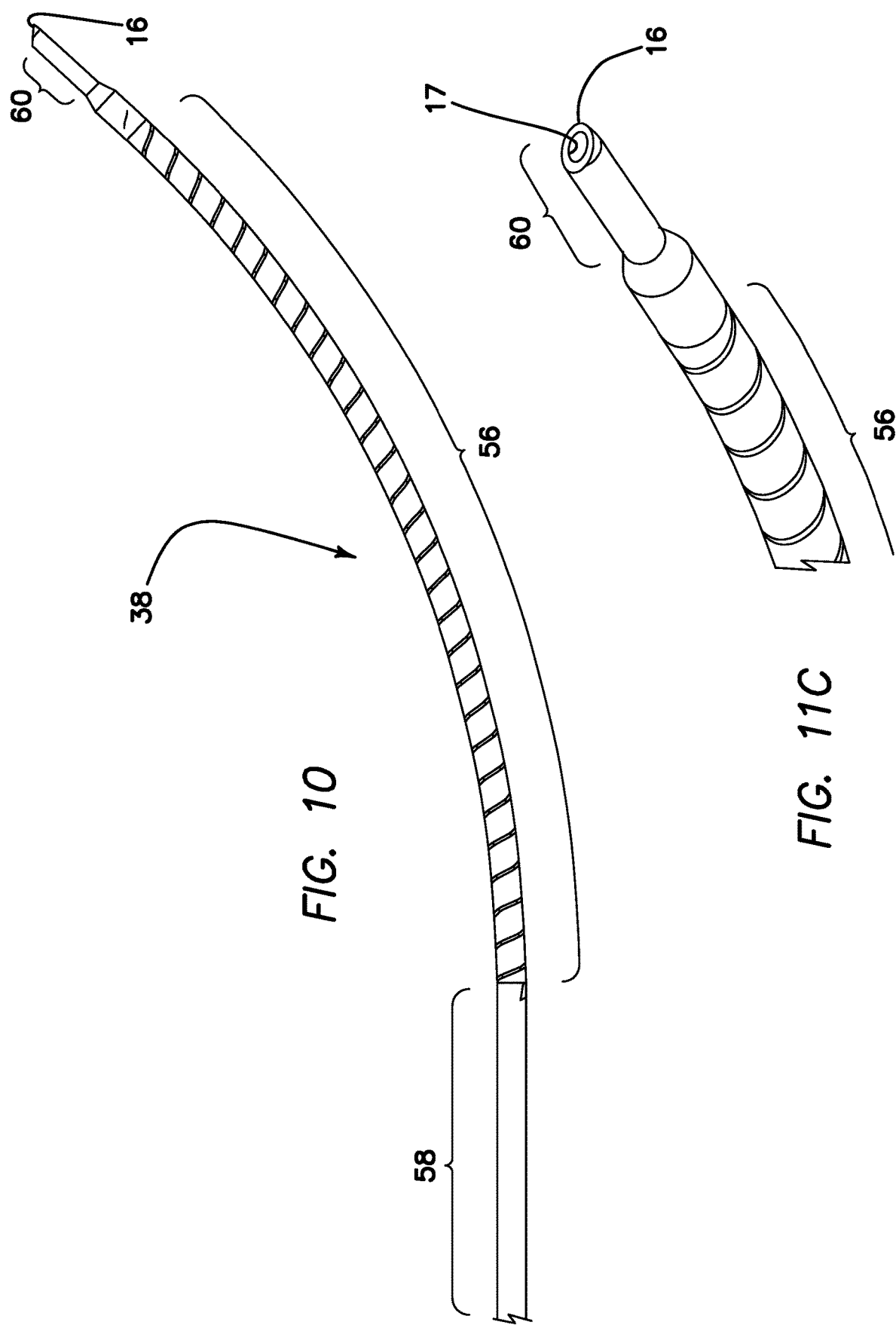

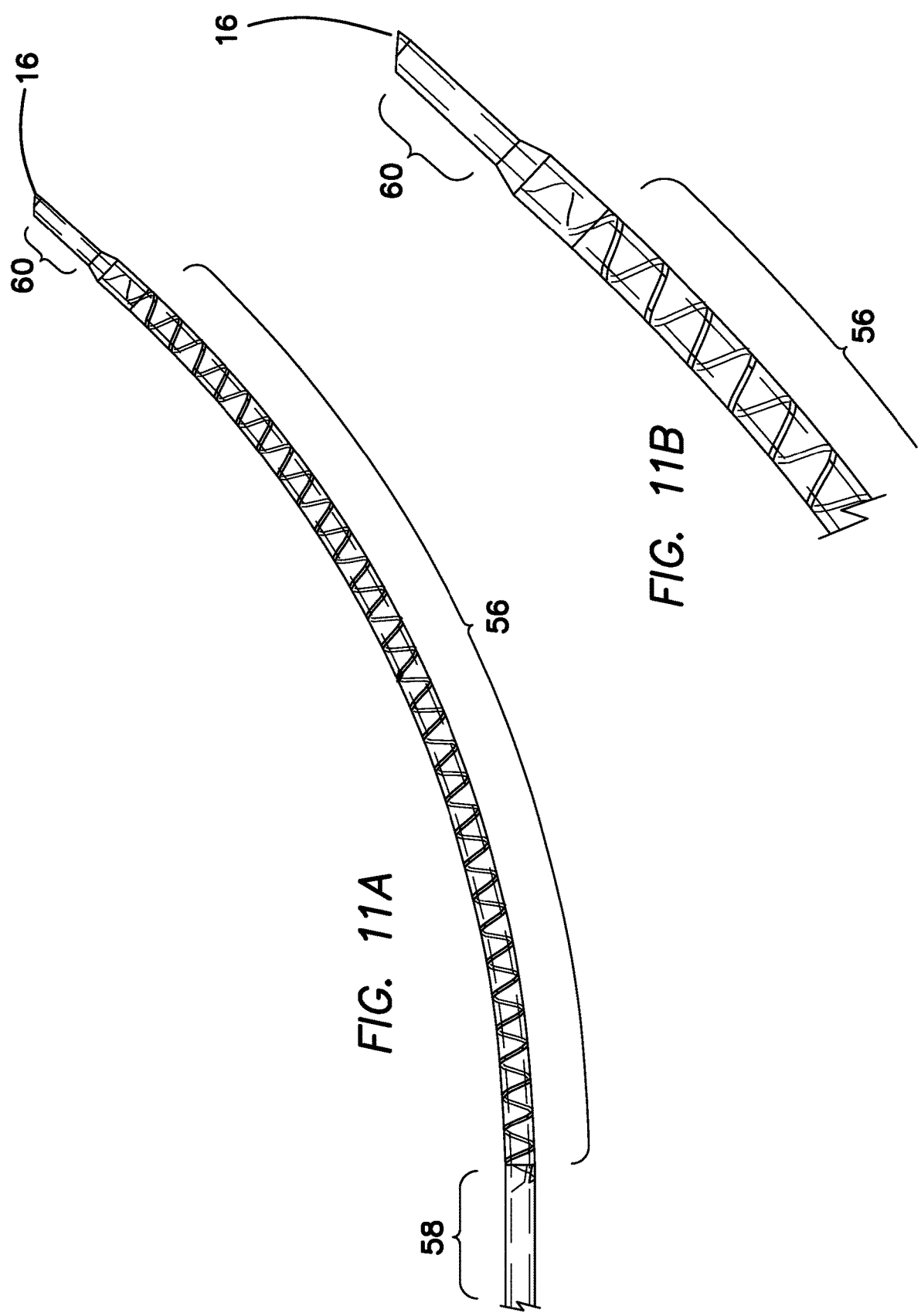

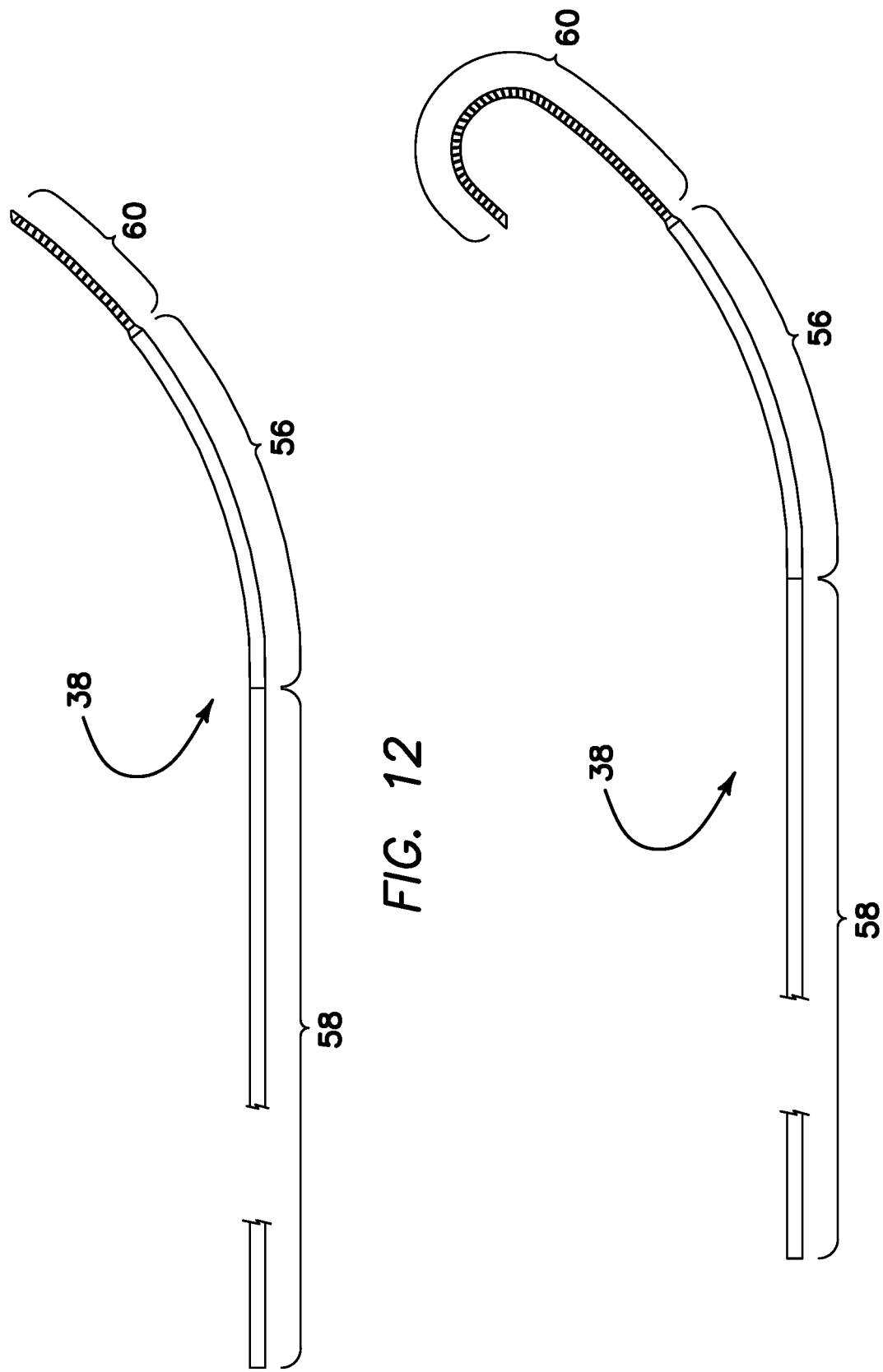

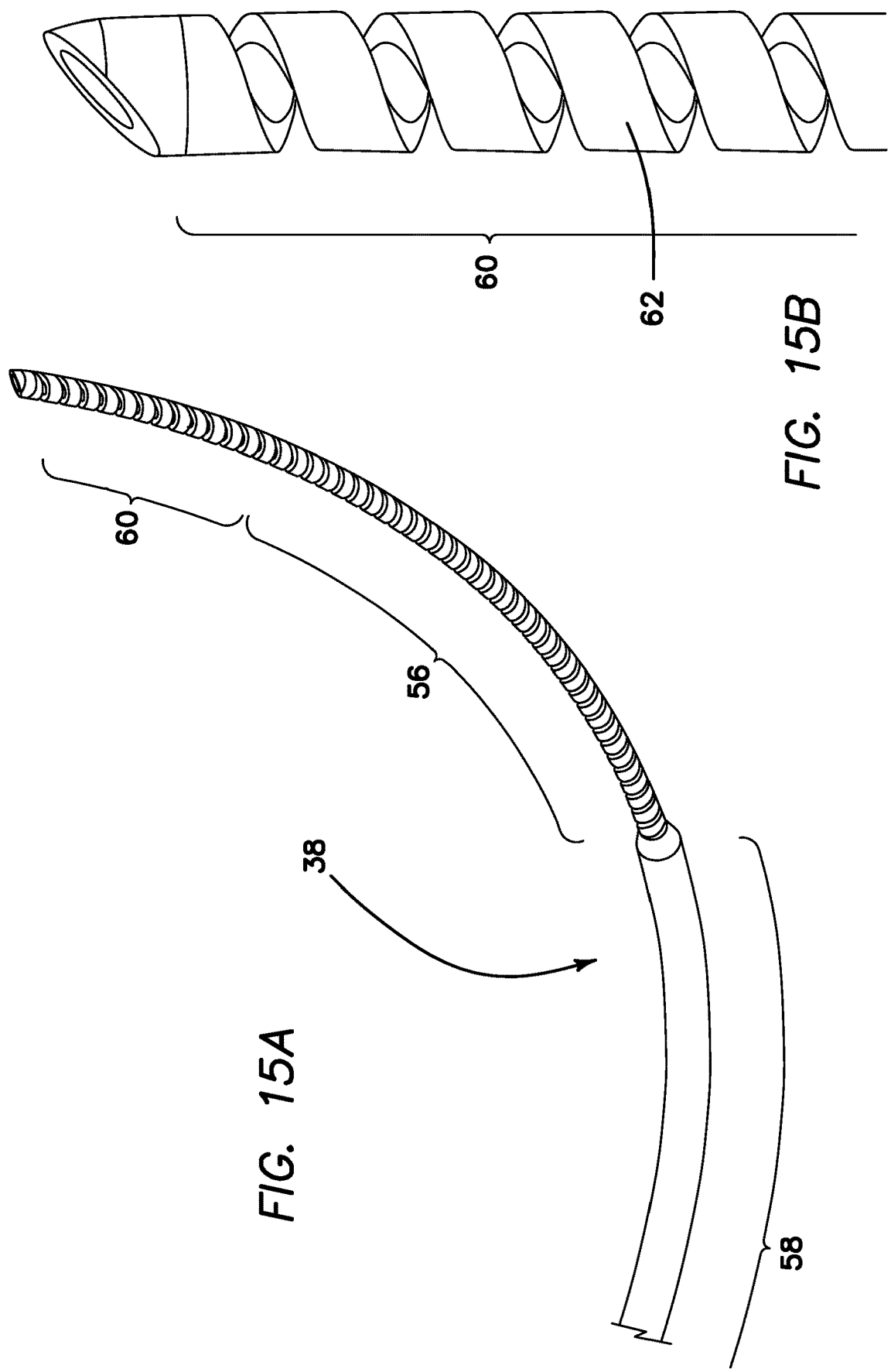

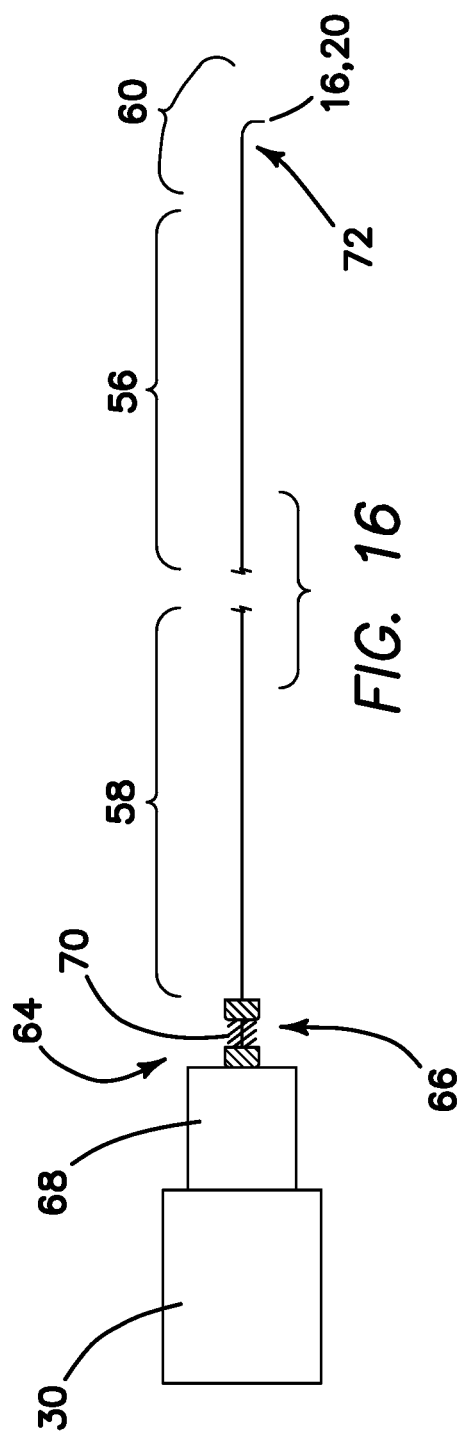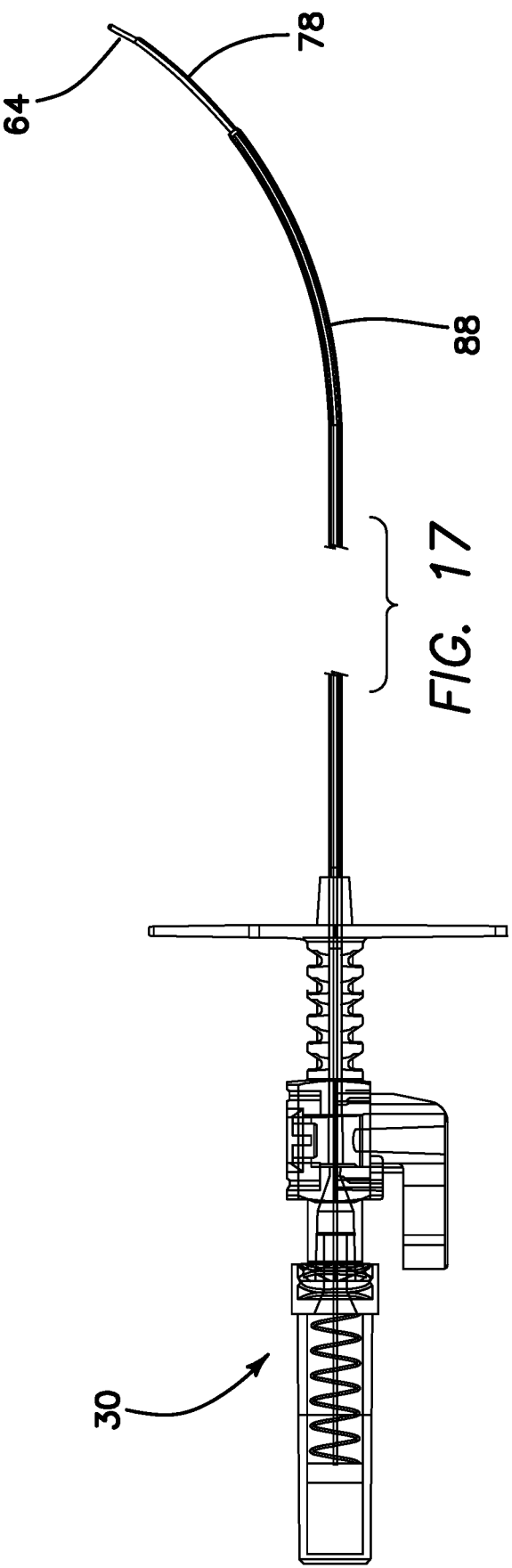

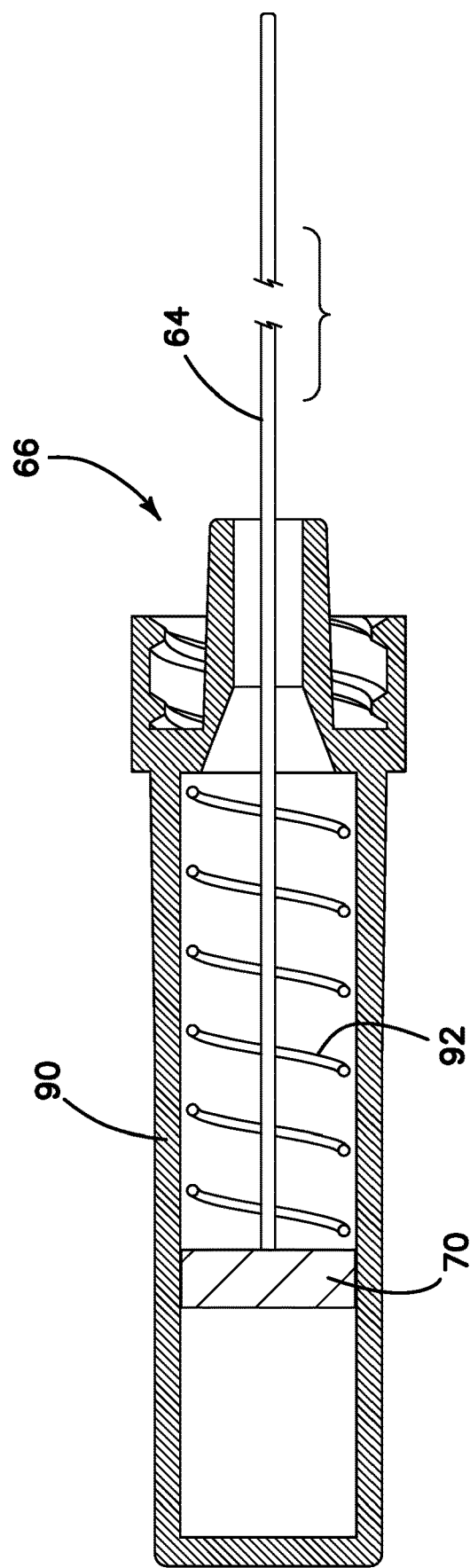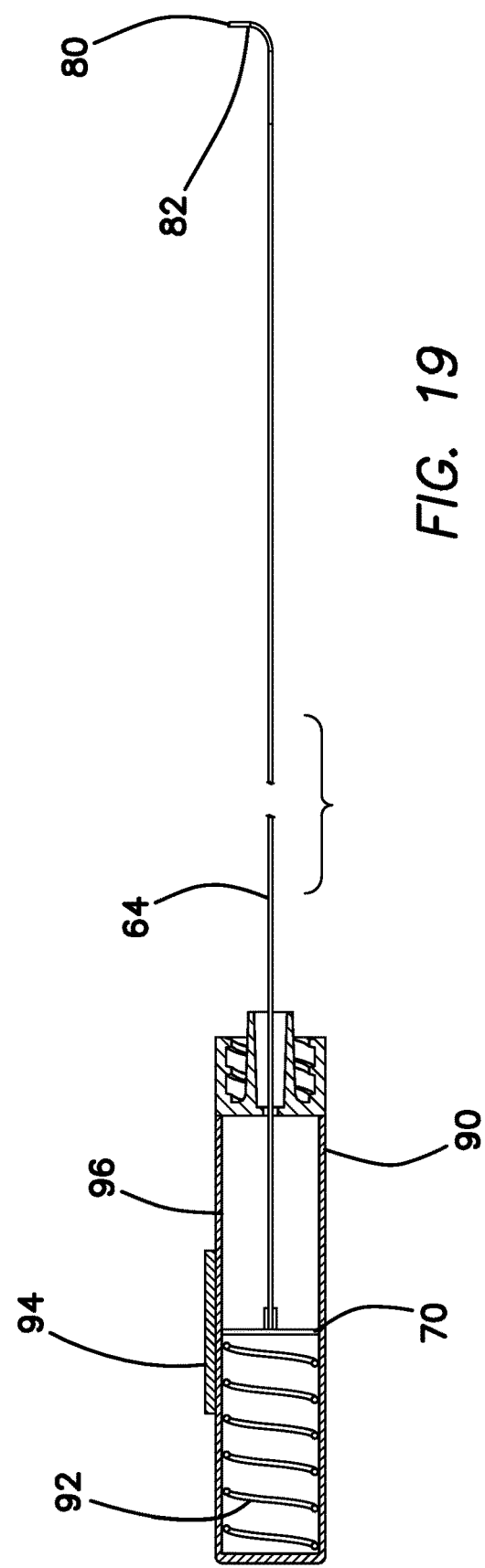

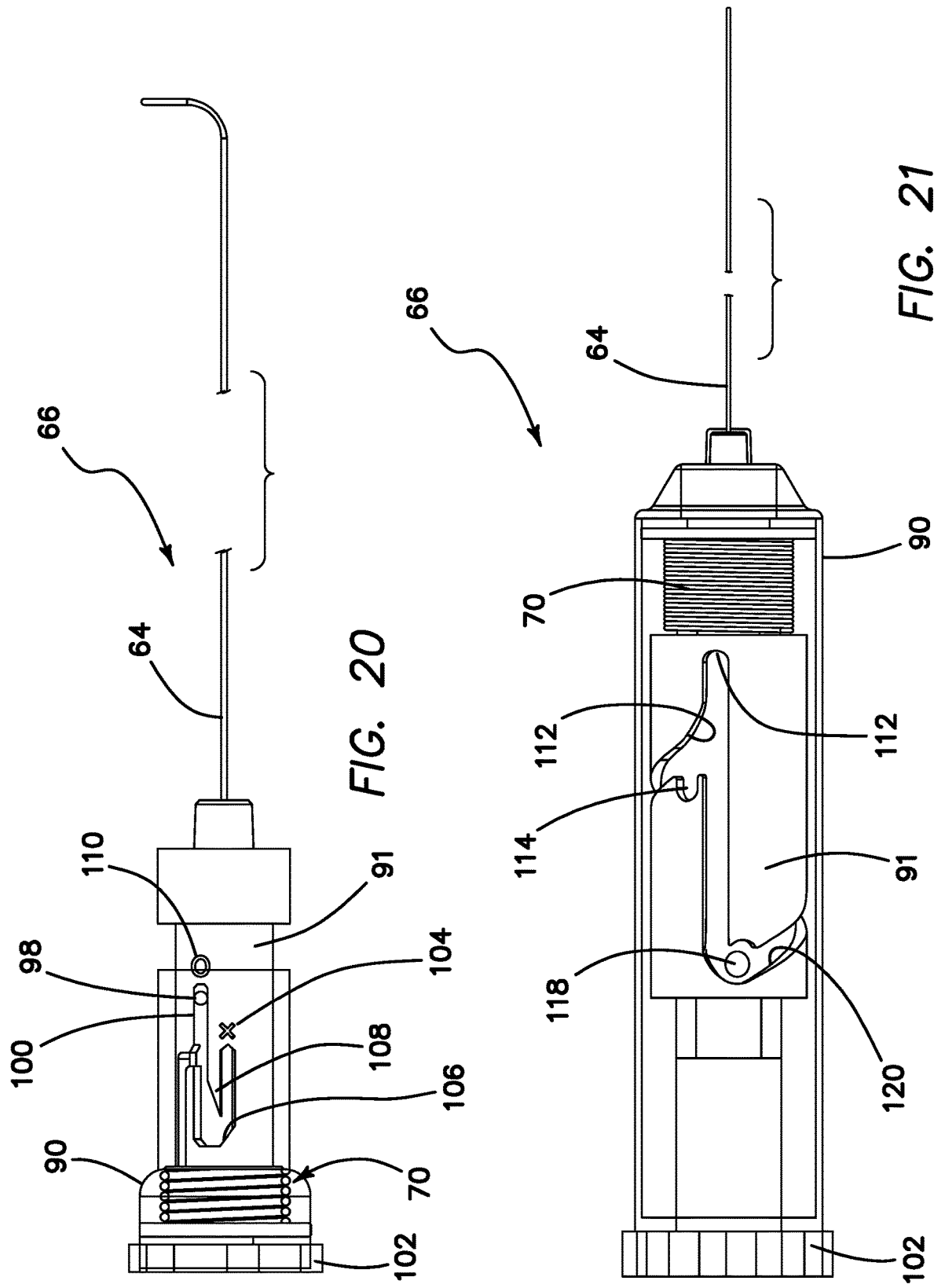

CARDIAC TRANSSEPTAL INSTRUMENTS, ASSEMBLIES, AND METHOD OF USE OF THE SAME

BACKGROUND

This application claims priority to, and the benefit of the earlier filing date of US non-provisional patent application entitled "IMPROVEMENTS IN CARDIAC TRANSSEPTAL INSTRUMENTS, ASSEMBLIES, AND METHOD OF USE OF THE SAME", filed on Jan. 21, 2020, Ser. No. 16/748,610, pursuant to 35 USC 120, the contents of all of which are incorporated herein by reference.

FIELD OF THE TECHNOLOGY

The invention relates to the field of transseptal puncture apparatus, assemblies, and methods, such as included within International Classes A61B 17/34; A61M 25/01; A61M 25/09; A61B 17/00; A61B 17/06; A61B 17/22; A61M 5/178; and A61M 5/32.

DESCRIPTION OF THE PRIOR ART

Transseptal puncture needles and transseptal puncture needle assemblies are well known, and more specifically, curved transseptal puncture needles and needle assemblies that facilitate insertion through curved transseptal introducers to minimize skiving the interior lumen of the introducer have been developed. One example of such a needle assembly is disclosed by Gurusamy, U.S. Pat. No. 7,635,353. The needle tip is shown in FIG. 29 of that patent and is defined by a needle tip with one of several different complex configurations, called a tangential back bevel, a reverse tangential back bevel, or a conical reverse bevel. Another example is disclosed by Bednarek, U.S. Pat. No. 8,114,110. The needle tip as shown in FIGS. 16-19 provide an "extra sharp" version of the Gurusamy needle tip. The configurations contemplate compound or complex multifaceted surfaces and are difficult to manufacture consistently in needle tips without undertaking costly manufacturing processes. What is needed is a design that can readily and inexpensively be manufactured with high precision in the material specifications relevant to puncture capability and antiskiving performance.

Moreover, in addition to a needle assembly which does not skive the interior lumen of the introducer, it is desirable that the needle can cross or penetrate the septal wall without undue resistance or tenting of the septal wall. The fibrousity and thickness of the septal wall may vary considerably from one patient to another, and it is desirable that the transseptal needle assembly be able to easily or controllably puncture the septal wall regardless of patient variability. Hence, what is needed is some kind of design which allows for ease of puncture of septal walls of varying fibrousity or thickness, or which design allows for different degrees of sharpness of the needle tip.

One of the common considerations in transseptal needle design is the safety of the use of the needle assembly during the penetration of the septal wall. If after the needle punctures the septal wall, and it has a configuration that may damage or puncture the opposing wall of the left atrium, undue hazard may be associated with the design. Moreover, it the needle encounters enough resistance to puncturing the septal wall such that the septal wall is tented by the advancing introducer or needle, the septal wall may suddenly rebound when puncture is achieved with the result that the position of the needle tip is briefly uncontrolled and ends in an unintended position or causes cardiac damage. In addition to cost and ease of manufacture and good puncture performance, controllability of the puncture and the assumption of an atraumatic configuration of the needle tip once puncture is achieved is desirable as well.

What is needed is some kind of a design that does not skive the introducer, that is inexpensive and which can be consistently be manufactured with high precision, which has high puncture performance, and which is atraumatic once puncture is achieved.

BRIEF SUMMARY

The current invention provides a hollow needle assembly for a transseptal cardiac needle. The hollow needle assembly includes a distal portion, a proximal portion, and a spring mechanism that coupled to the hollow needle assembly such that the spring mechanism is loaded when the hollow needle assembly is advanced against a predetermined position on a septal wall. The spring mechanism is unloaded after the transseptal cardiac needle penetrates the septal wall allowing the distal portion of the transseptal cardiac needle to extend unsupported and thereby assume an atraumatic configuration. The distal portion of the transseptal cardiac needle is comprised of material that is more flexible relative to the proximal portion.

In one embodiment, the distal portion of the transseptal cardiac needle includes a spiral structure which provides it with increased flexibility as compared to the proximal portion. The distal portion of the transseptal cardiac needle includes a defining wall and where the spiral structure comprises thinning the defining wall of the distal portion in a spiral pattern. Alternatively, the distal portion of the transseptal cardiac needle is comprised of a spiral wrap. Specifically, the distal portion of the transseptal cardiac needle may have a predetermined curve defined therein.

In another embodiment, the distal portion of the transseptal cardiac needle includes a defining wall and where the structure comprises thinning the defining wall of the distal portion.

In a further embodiment, the distal portion of the transseptal cardiac needle includes an inherently flexible material. Specifically, the inherently flexible material may be nitinol.

In another embodiment, the hollow needle assembly for a transseptal cardiac needle also includes a stylet coupled to the spring mechanism such that the spring mechanism is loaded when the stylet is advanced against a predetermined position on a septal wall, and where the spring mechanism is unloaded after the transseptal cardiac needle penetrates the septal wall allowing the distal portion of the transseptal cardiac needle to extend unsupported and thereby assume an atraumatic configuration.

In a further embodiment, the transseptal cardiac needle includes a bird beak tip, where the bird beak tip itself includes an inner surface and an outer surface. More specifically, the bird beak tip has a longitudinal axis and a leading edge of the bird beak tip, where the leading edge of the bird beak tip is located at and adjacent to the distal end of the inner and outer surfaces. The inner surface of the hollow transseptal cardiac needle defines an opening of the bird beak tip and the distal end of the bird beak tip is curved relative to the longitudinal axis of the hollow transseptal cardiac needle into the opening of the bird beak tip.

In another embodiment, the stylet includes a distal portion and a proximal portion, where the distal portion is comprised of material that is more flexible relative to the proximal portion.

In an additional embodiment the transseptal cardiac needle includes a tip which in turn includes an inner surface of the needle, an outer surface of the needle, where the inner and outer surfaces of the needle have a common longitudinal axis, a bevel provided on a distal end of the needle to define a face of the needle, and a pair of opposing side bevels defined into a distal end of the face of the needle, the side bevels intersecting at the distal end of the needle to define the needle tip. The distal end of the needle and the needle tip bends toward the longitudinal axis of the needle.

The current invention also provides a method of using a spring mechanism coupled to an elongate stylet or needle for a transseptal cardiac procedure. The method includes providing a stylet or needle comprising a distal portion and a proximal portion, where the distal portion is flexible relative to the proximal portion, disposing the stylet or needle into an atrium in a heart oriented toward a selected position against a septal wall, the stylet or needle being coupled to the spring mechanism, and then advancing the stylet or needle against the selected position on the septal wall while tenting the septal wall and while spring loading the spring mechanism. Next, the spring mechanism is automatically unloaded as the stylet or needle penetrates the septal wall allowing the stylet or needle to extend unsupported into an opposing atrium and to assume an atraumatic configuration.

In one particular embodiment, providing the stylet or needle comprising a distal portion and a proximal portion includes providing the distal portion with a spiral structure.

In a related embodiment, providing the stylet or needle comprising a distal portion and a proximal portion includes providing the distal portion with a spiral wrap.

In a further embodiment, providing the distal portion with a spiral structure includes thinning a defining wall of the distal portion in a spiral pattern.

In one embodiment, providing the stylet or needle comprising a distal portion and a proximal portion comprises providing a distal portion that is comprised of an inherently flexible material. Specifically, the distal portion may be comprised of nitinol.

In an additional embodiment, the method also includes locking the spring mechanism so that the stylet is fixed in position relative to the needle and serves to atraumatically prevent advancement of the needle into heart tissue.

In another embodiment, the method also includes emitting a visual, audible, or tactile response from the spring mechanism to indicate when the stylet or needle is tenting the septal wall and/or when the needle has perforated the septal wall.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 2a is a side elevational view of a prior art B-bevel needle tip of FIG. 1a.

FIG. 2b is a top elevational view of the needle tip of FIG. 1a.

FIG. 2c is a side perspective view of the needle tip of FIG. 1a

FIG. 2d is a top perspective view of the needle tip of FIG. 1a

FIG. 3b is a top elevational view of the needle tip of FIG. 1b.

FIG. 3c is a side elevational view of the needle tip of FIG. 1b

FIG. 4 is an overall side elevational view of the curved transseptal needle assembly of the improved embodiments.

FIG. 5 is an enlarged longitudinal cross sectional view of the distal portion of the needle assembly of FIG. 4

FIG. 6a is a side cross sectional view of the distal portion of transseptal puncture device depicted in FIG. 1a being inserted into a curved transseptal dilator.

FIG. 6b is a side cross sectional view of the distal portion of a curved transseptal puncture device having a "bird beak" tip configuration depicted in FIG. 1b being inserted into a curved transseptal dilator.

FIG. 7 is an overall side view of the transseptal puncture device with two-piece design with the distal portion shown in side cross sectional view.

FIG. 10 is a side view of the distal portion of a transseptal puncture device embodiment wherein the intermediate portion of the needle is provided with flexible properties.

FIG. 11a is a side cross sectional view of the distal portion of an embodiment wherein an intermediate portion of the needle is constructed with a predetermined flexibility.

FIG. 11b is an enlarged side cross sectional view of the distal portion of the embodiment of FIG. 11a.

FIG. 11c is an enlarged perspective view of the distal portion of the embodiment of FIG. 11a.

FIG. 12 is a side elevational view of an embodiment wherein the distal portion of the needle is constructed with a predetermined flexibility.

FIG. 13 is a side view of the distal portion of an embodiment of a transseptal puncture device similar to FIG. 12, wherein the distal tip, not the intermediate portion, is manufactured or formed from a material such that it is more likely to bend than the proximal portion.

FIG. 15a is a side elevational view of the distal portion of an embodiment in which the distal portion of the needle is fabricated with a ribbon-spiral structure to give it flexibility without loss of columnar strength when confined within the introducer.

FIG. 15b is a side perspective view of the distal portion of the needle of the embodiment of FIG. 15a.

FIG. 16 is a side elevational view of a sharp needle and spring stylet assembly.

FIG. 17 is a side view of an assembly including a stylet and bird beak tipped needle.

FIG. 18 is a side cross sectional view of a spring mechanism coupled to the stylet of FIG. 17-17c, FIG. 19 is a side cross sectional view of another embodiment of the spring mechanism incorporating a lockable slider coupled to the stylet.

FIG. 20 is a side plan view of another embodiment of the hub assembly and spring mechanism coupled to a stylet.

FIG. 21 is a side plan view of yet another embodiment of the hub assembly and spring mechanism coupled to a stylet.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1A:
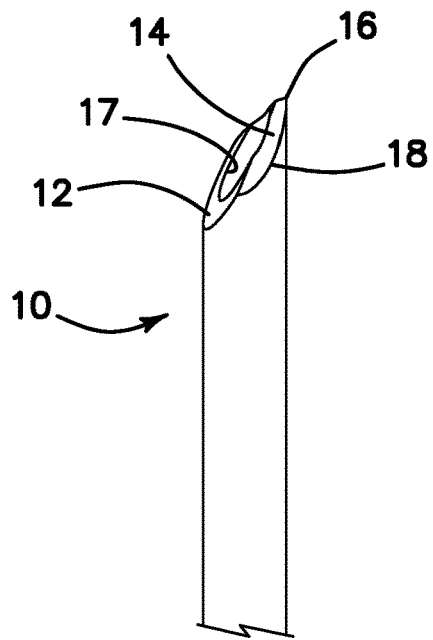
FIG. 1a is a side perspective view of a prior art needle tip having a standard B-bevel needle tip.
Figure 1B:
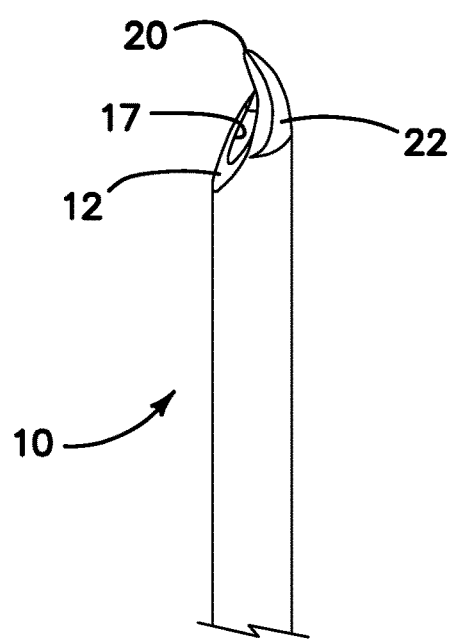
FIG. 1b is a side perspective view of a needle tip having a reverse back bevel which is contoured toward the opposing side of the needle tip and is referenced herein as a "bird's beak" needle tip.
Figure 2A:
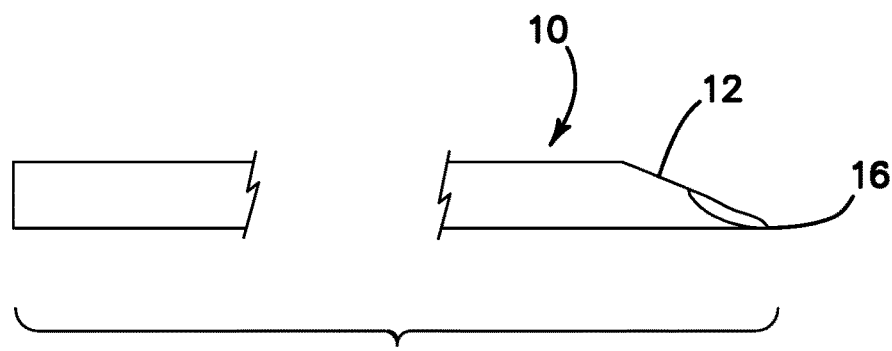
Figure 2B:
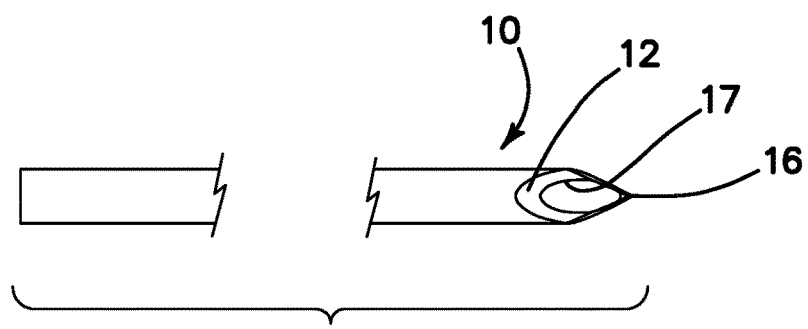
Figure 2C:
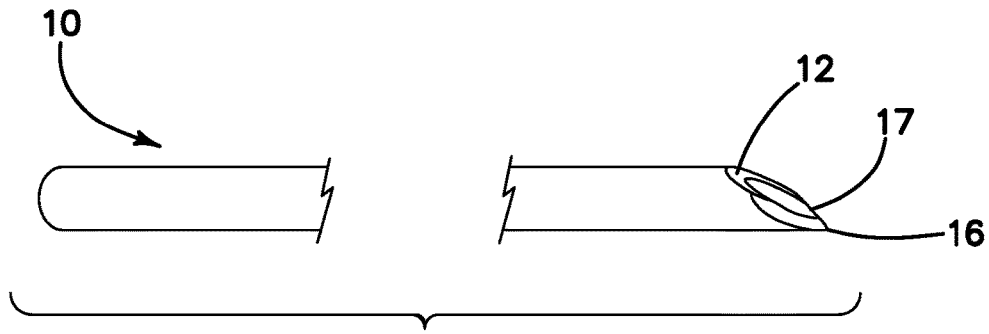
Figure 2D:
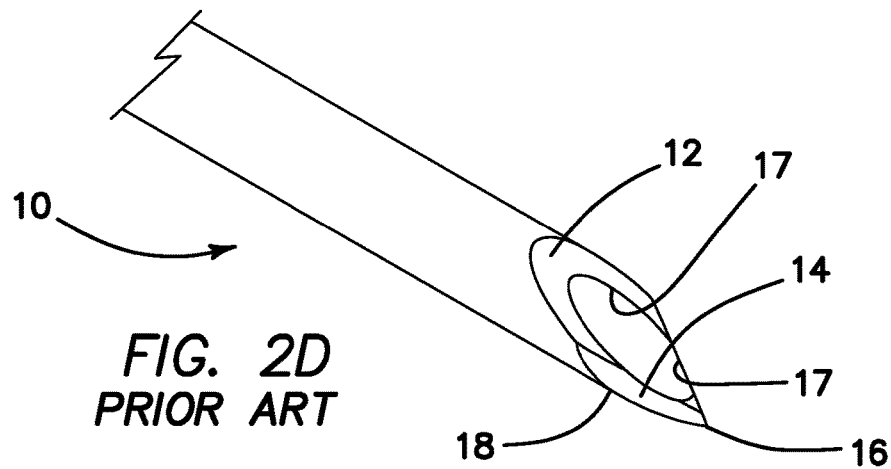
Figure 27A:
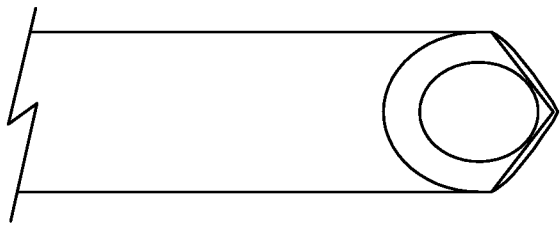
FIGS. 27a-27c are top plan, side plan and perspective views respectively of one embodiment of the prior art Gurusamy needle tip shown in U.S. Pat. No. 8,114,110.
Figure 27B:
Figure 27C:
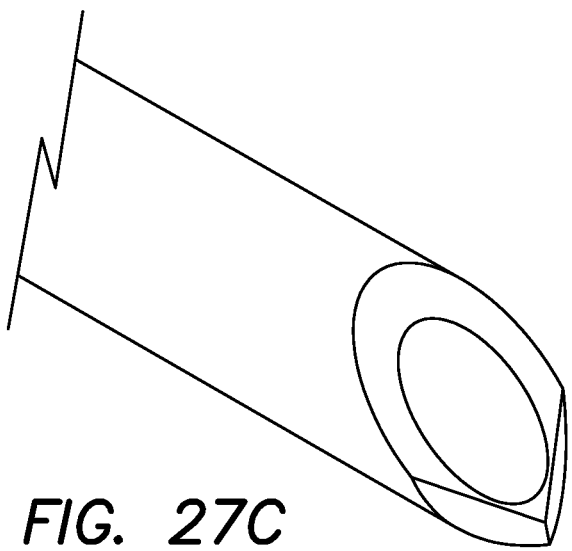
Figure 28A:
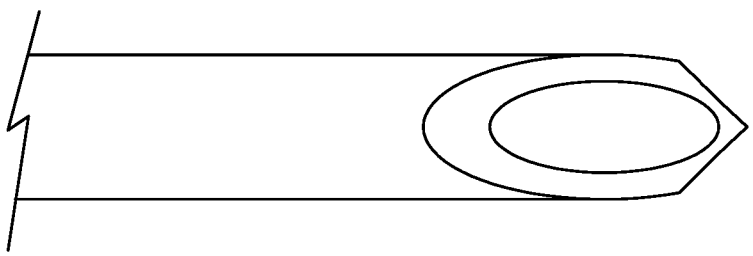
FIGS. 28a-28d are top plan, side plan, bottom plan view and perspective views respectively of another embodiment with a back bevel of the prior art Gurusamy needle tip shown in U.S. Pat. No. 8,114,110.
Figure 28B:
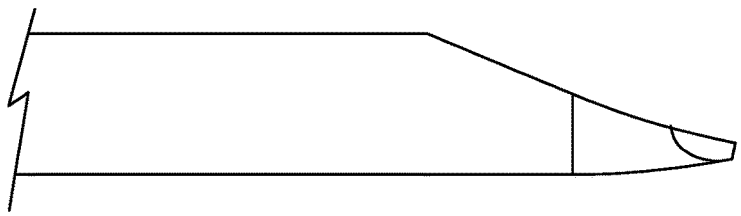
Figure 28C:
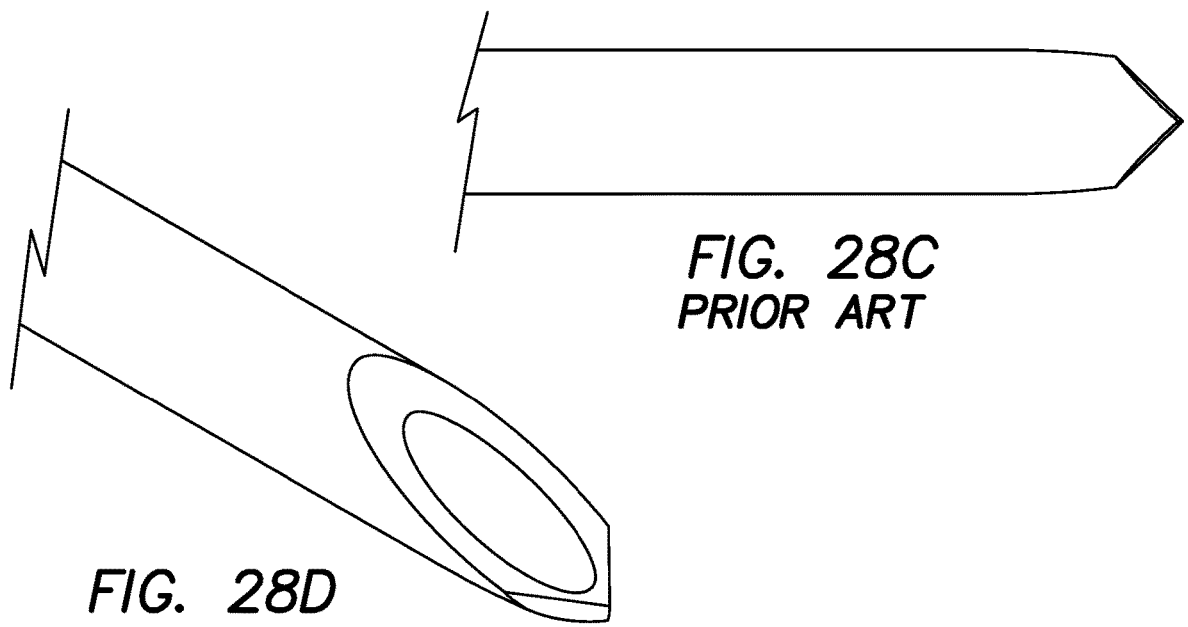
Figure 28D:
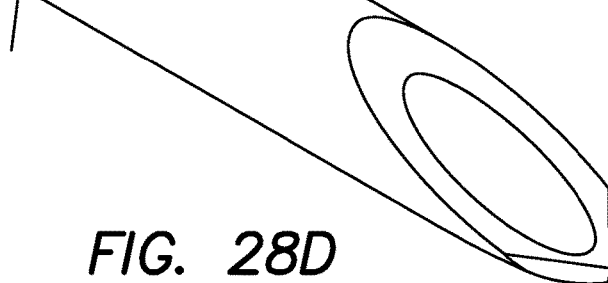

FIG. 1a depicts a needle tip 10 having a prior art configuration with a B-bevel configuration, comprising a primary bevel 12 of approximately 18 degrees off the vertical, l, left and right tangential bevels 14 defining tip 16. The needle tip 10 includes the puncture tip leading edge 16 and a wedge surface defined by bevel 12, which in the views of FIGS. 2b and 2d can be seen to comprise two disconnected surface segments. The defining tip 16 is approximately radially aligned with the cutting or leading edge 17 at the inner diameter of needle tip 10 defined by the primary bevel 12, so that the bird's beak needle 10 is noncoring. FIG. 1b depicts a needle tip 10 having the "bird beak" configuration, comprising a tangential back bevel configuration having some elements in common with the design of FIG. 1a, but wherein a conventional A-Bevel, B-Bevel, or C-Bevel puncture tip has been bent inward or toward the opposing side of the needle tip 10 to provide a contoured surface 22. The needle exhibits a sharp pointed tip that is curved towards the opening of the hollow needle creating an offset of the pointed tip from the outer surface of the hollow needle and an offset of the pointed tip from the inner surface of the hollow needle. An A-Bevel puncture tip typically has a primary bevel angle of 12 degrees from vertical, a B-Bevel puncture tip typically has a primary bevel angle of 18 degrees from vertical, and a C-Bevel puncture tip typically has a primary bevel angle of 30 degrees from vertical as defined in detail in the Federal Specification GG-N-196, now obsolete. Similar needle tip designs can be found in ISO 7864. As the primary bevel angle is lowered, the inherent puncture force is lowered. Table 1 provides a comparison of puncture forces for various embodiments normalized to the puncture force of a standard transseptal needle comparing the "bird beak" offset pointed tip configuration with a b-bevel as compared to a standard and "extra sharp" commercially available transseptal needle tip. Details of two embodiments of the extra sharp tip are better shown in FIGS. 27a-27c and in FIGS. 28a-28d for a tip with a back bevel as shown in U.S. Pat. No. 8,114,110. This embodiment decreases the risk of scraping along the inner surface of the introducer (not shown) into which the needle tip 10 is inserted, while maintaining a sharp distal puncture tip 20 to allow for easy puncture through tough and/or fibrous septa of the heart.

TABLE 1

Figure 9A:
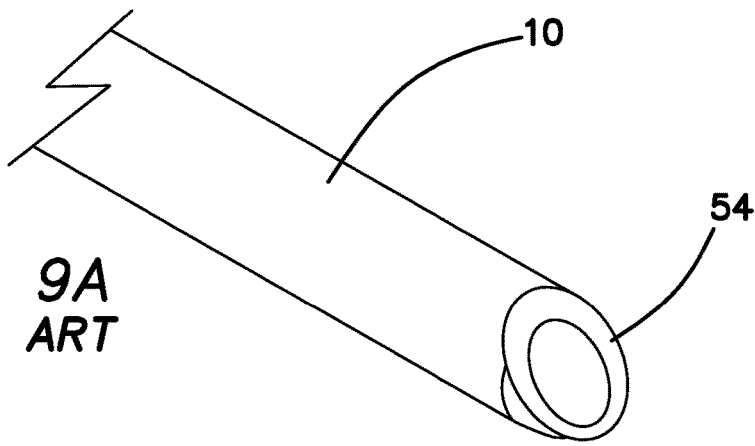
FIG. 9a is a three quarter perspective view of a conventional back beveled needle tip such as shown in FIG. 29 of Gurusamy et.al., U.S. Pat. No. 7,635,353 incorporated herein by reference.
Figure 9B:
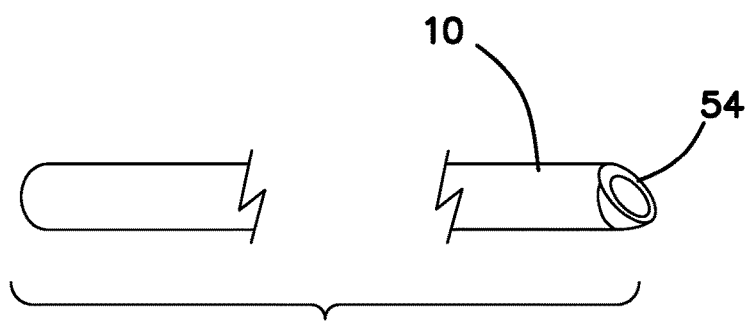
FIG. 9b is a side perspective view of a conventional back beveled needle tip such as shown in FIG. 29 of Gurusamy et.al., U.S. Pat. No. 7,635,353.
Figure 9C:
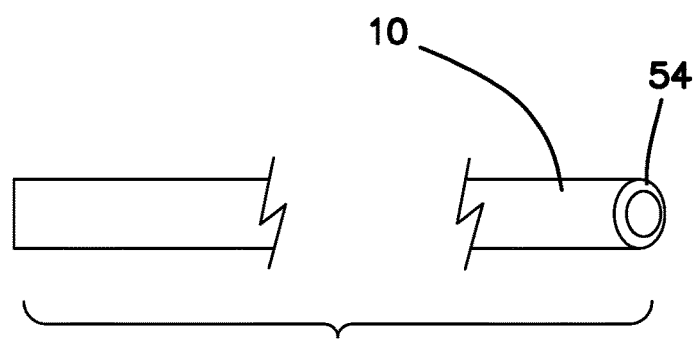
FIG. 9c is a top perspective view of a conventional back beveled needle tip such as shown in FIG. 29 of Gurusamy et.al., U.S. Pat. No. 7,635,353.
Figure 9D:
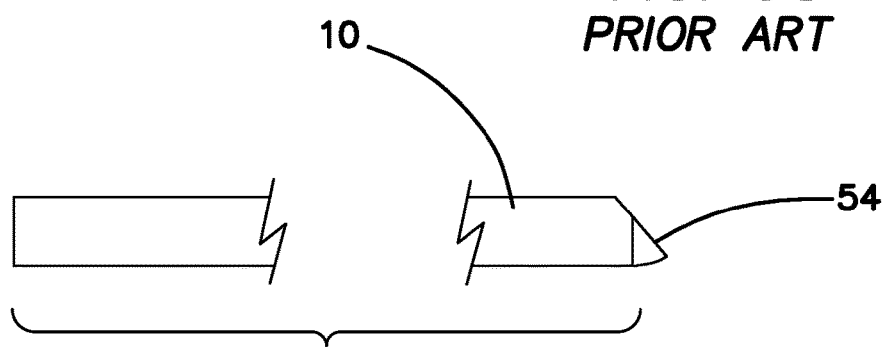
FIG. 9d is a side elevational view of a conventional back beveled needle tip such as shown in FIG. 29 of Gurusamy et.al., U.S. Pat. No. 7,635,353.

| Description | Insertion Force (percentage) |
| --- | --- |
| Prior art standard transseptal (FIG. 9a) | 100% |
| Prior art extra sharp transseptal (FIGS. 27a-28d). | 62% |
| Bird Beak transseptal (FIG. 1b) | 28% |

Figure 3A:
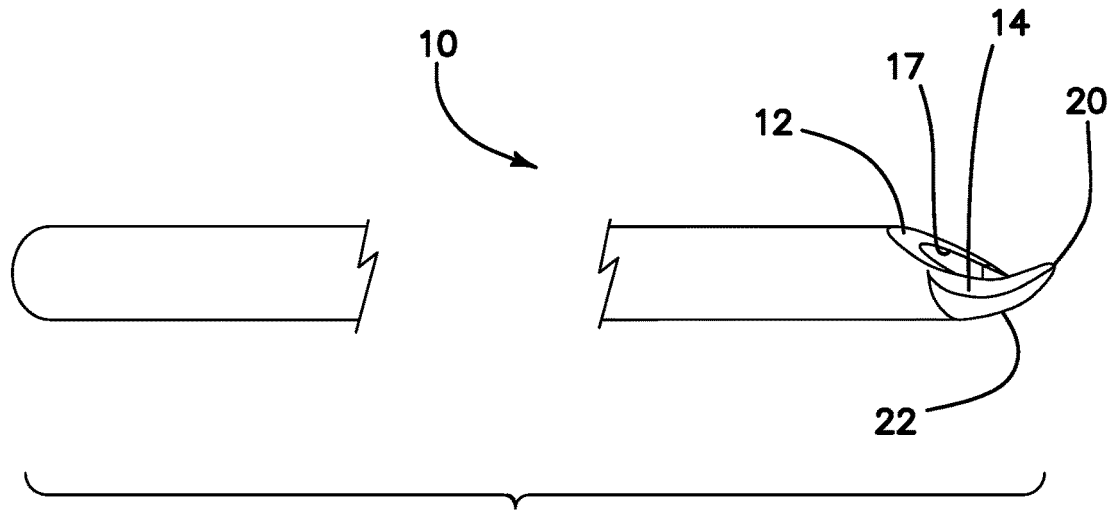
FIG. 3a is a side perspective view of the needle tip of FIG. 1b.

In the cannula-insert assembly 24 of FIG. 4 and as better seen in the enlarged partial view of FIG. 5, a cannula 26 is used inside a dilator 40 (FIG. 6a) to shape the curved transseptal introducer 32 (FIG. 6a) and provide it with columnar support. At its proximal end the cannula 26 is fit into a hub and handle assembly 30, which is used to direct the insertion of the cannula-insert assembly 24 into an introducer 32 shown in FIGS. 6a and 6b. At the distal end of the cannula 26, an insert 34 is fed into the inner lumen of cannula 26. The distal end of insert 34 is provided with a configuration as shown in FIG. 4 and extends beyond the cannula's distal end to act as the puncture leading edge. Insert 34 integrally includes the tip 16 or 20 of needle 10, or the tip 16 or 20 may be a two-part construction with insert 34. The insert 34 is fixed in place within the cannula 26 lumen by means of a crimped area 36, wherein the cannula wall has been compressed inward with small detents on all sides such that small folds or ridges form to grip the outer wall of the insert 34. Crimping is an economic, quick and reliable means of joining tubular elements, particularly if made of different materials. In this manner, an expensive distal element for needle 10 can be joined to a less expensive insert 34, or a less expensive cannula 26, thereby materially simplifying and reducing the cost of the cannula-insert assembly 24 The cannula-insert assembly 24 is then shaped with a distal curvature to fit the desired anatomy in the heart. The "bird beak" embodiment of FIG. 3c is also easily constructed by starting with a beveled needle tip with the desired primary bevel angle and "bending" the needle tip inward towards the bevel heel. This operation requires precision tooling or a die as the amount of bend as discussed in connection with FIG. 30 below is critical to maintain low puncture forces while preventing skiving of the introducer.

Figure 30:
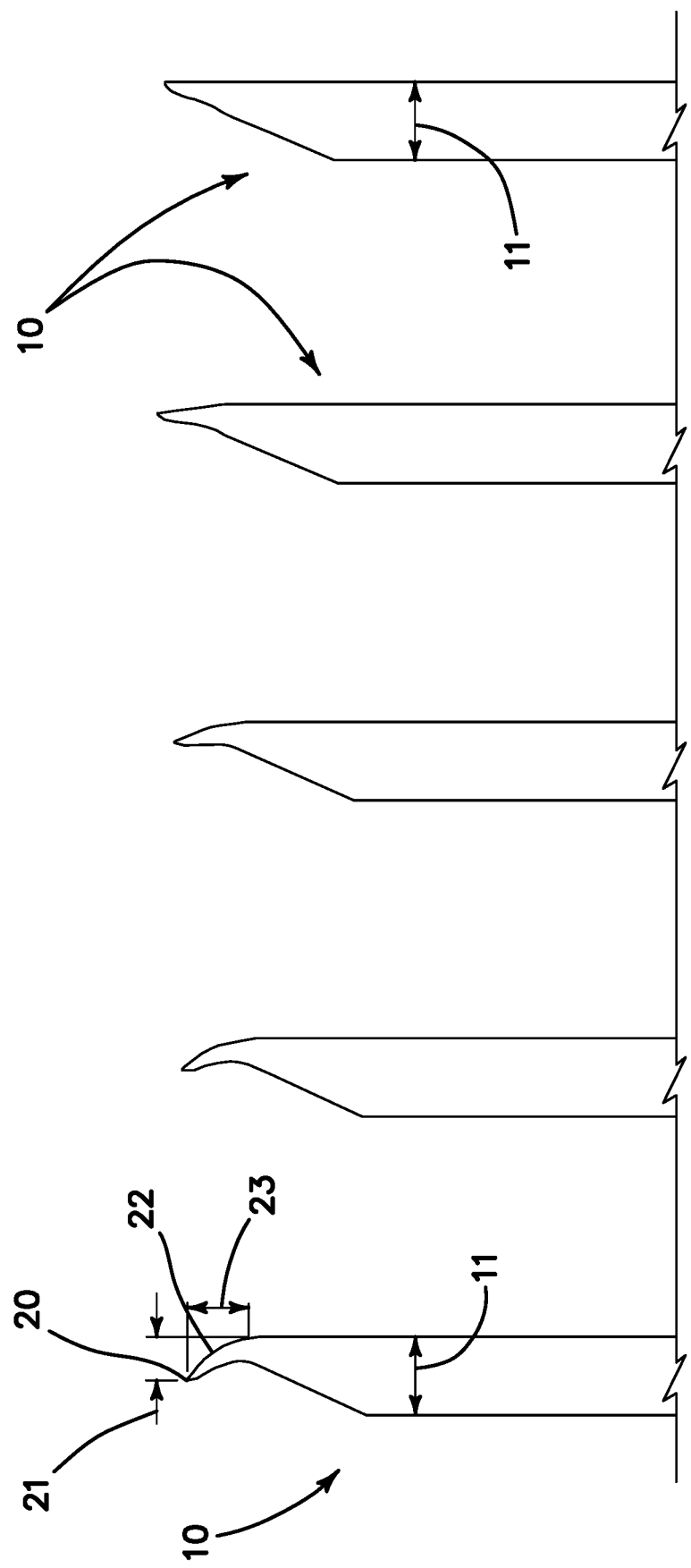
FIG. 30 is a side plan view of a sharpened or hypodermic needle showing a series of steps wherein the tip of the needle is formed into a predetermined bird's beak with a specifically defined tip offset and tip offset length.

FIG. 30 is a side plan view of a sharpened or hypodermic needle showing a series of steps wherein the tip of the needle is formed into a predetermined bird's beak with a specifically defined tip offset and tip offset length. Needle tip 10 is formed in a hollow needle with an outer diameter 11 as best shown in the rightmost depiction in FIG. 30. A die, not shown, defining a predetermined curvature is disposed on needle 10 and by forming a selected one of predetermined curvatures on needle 10 as suggested by the series of side views of needle 10 in FIG. 10 moving from right to left. Ultimately, a predetermined shape or curvature of needle 10 is formed having a puncture tip 20 and contoured surface 22. The tip offset 21 from the forward most extension of puncture tip 20 to the back surface of needle 10 is in one embodiment defined to be a minimum of 0.010 inch (0.254 mm) and a maximum of one half the outer diameter 11 of needle 10. The tip offset 23 is defined as the distance in vertical projection from the base of contoured surface 22 where it just begins to curve to the puncture tip 20.

Figure 29A:
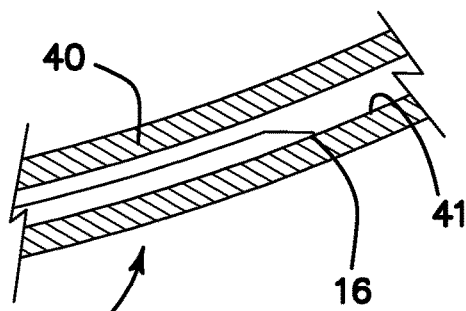
FIG. 29a is an enlarged side cross sectional view of the curved transseptal puncture device with prior art configuration inserted into a transseptal introducer.
Figure 29B:
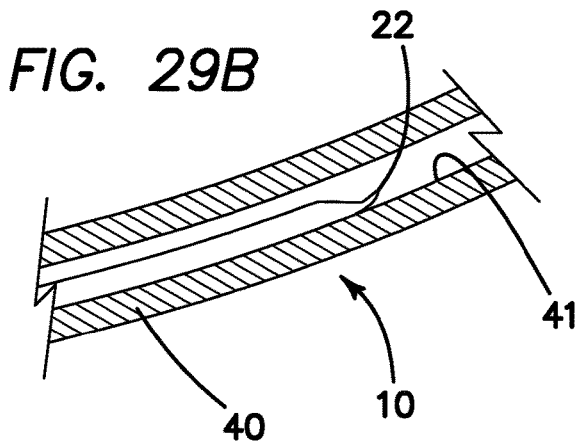
FIG. 29b is an enlarged cross sectional view of the curved transseptal puncture device with the novel configuration of the bird's beak.

The operation and advantages of the needle tip 10 of FIG. 30 is illustrated by comparison of FIGS. 29a and 29b. FIG. 29a is an enlarged side cross sectional view of the curved transseptal puncture device 10 of FIG. 1a with prior art configuration inserted into a transseptal introducer. The straight sharp tip 16 is shown skiving the inner wall 41 of the dilator 40. FIG. 29b is an enlarged cross sectional view of the curved transseptal puncture device 10 of FIG. 1b with the configuration of the bird's beak. The tip 20 is bent inward relative to the longitudinal axis of the needle 10, thereby offsetting the tip 20 from the inner wall 41 of the dilator 40. This bend decreases the chance of skiving because the tip 20 does not catch on the dilator 40.

FIG. 6a is a side cross sectional view of the distal portion of a curved transseptal puncture device 38 having the prior art tip configuration depicted in FIG. 1a being inserted into a curved transseptal introducer 32, comprised of a sheath (not shown) and a hollow dilator 42. The dilator 42 has a convex side 44 and a concave side 46 as well as a defined curvature that is meant to match the curvature of the anatomy in which it is used. As the needle 10 is advanced through the dilator lumen 48, a first side of the needle moves along the convex side 44 of the dilator 42. When the needle 10 is advanced into the curvature of the dilator 42, the puncture tip 16 leading edge of the prior art configuration may scrape along the inner surface of the convex side 46 of the dilator 42. As a result, the transseptal puncture device 38 is difficult to insert through the dilator 42 and is capable of shaving dilator material (skiving) from its inner surface. This material may then obstruct the lumen 48 of the dilator 42 or of the needle 10 or may dislodge into the patient.

FIG. 6b is a side cross sectional view of the distal portion of a curved transseptal puncture device 38 having the "bird beak" tip configuration depicted in FIG. 1b being inserted into a curved transseptal dilator 42 in the same manner as FIG. 6a above and as better depicted in FIGS. 29b and 30 below. Unlike the prior art version, this tip configuration is curved inward, so when the needle 10 is advanced through the lumen 48 of the dilator 42, the puncture tip 20 leading edge does not move along the inner surface of the convex side 44 of the dilator 42. The rounded surface of the back bevel behind and proximal from tip 20 resulting from the bending the tip 20 upward or toward the opposing side of needle 10 causes the puncture tip 20 leading edge to move unobstructed through the lumen 48 of the dilator 42 without contacting the inner surface of the dilator 42. This eases the advancement of the transseptal puncture device 38 and reduces the risk of shaving dilator material (skiving) which could enter into the patient.

The blunt end cannula 26 used inside the dilator 42 imparts a defined shape to the curved transseptal introducer 32 and provides it with columnar support. At its proximal end the cannula 26 is fitted into a hub and handle assembly 30, which is used to direct the insertion of the cannula-insert assembly 24 into the curved transseptal introducer 32. At the distal end of the cannula 26, an insert 34 is fed into its inner lumen 28. The distal end of this insert 34 is imparted with the configuration as discussed in FIG. 1a or 1b and extends beyond the cannula distal end to act as the puncture leading edge. As stated above, the insert 34 is fixed in place within the cannula inner lumen 28 by means of a crimped area 36, wherein the cannula wall has been compressed inward on all sides such that small folds or ridges form to grip the outer wall of the insert 34. While the illustrated embodiment utilizes a crimp as the structure of connection of insert 34 as the most economical and practical means of connection, it is also possible to join the insert 34 by gluing, soldering, welding, swaging or other equivalent means. The cannula-insert assembly is then imparted with a distal curvature to fit the anatomy in which the assembly will be used. This embodiment is similar to prior embodiments, but the two-piece crimping method of assembly significantly reduces manufacturing costs.

Figure 8A:
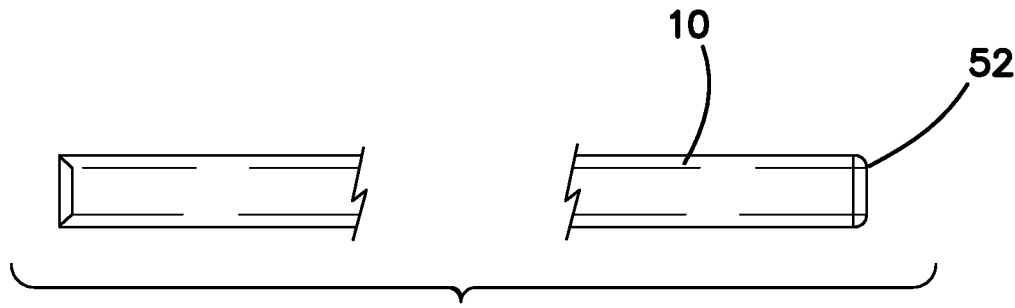
FIG. 8a is a side cross sectional view of a blunt needle tip.
Figure 8B:
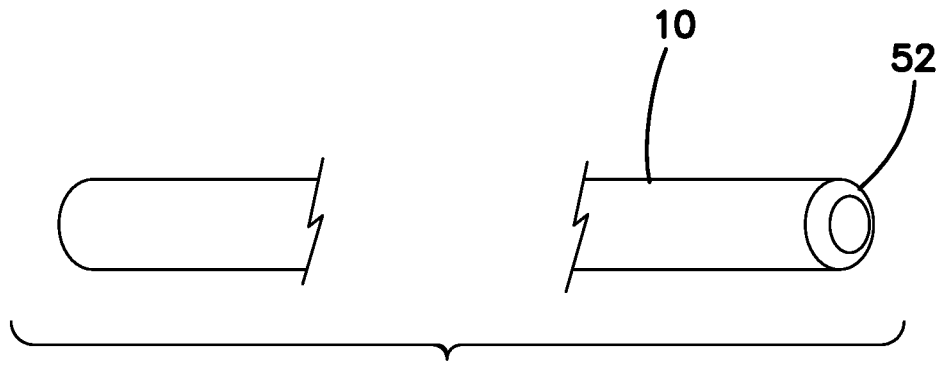
FIG. 8b is a side perspective view of a blunt needle tip.
Figure 8C:
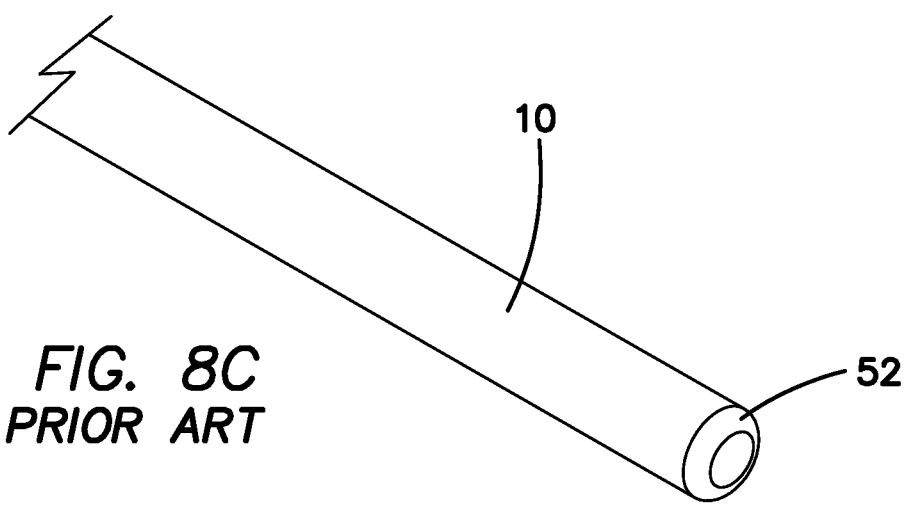
FIG. 8c is a three quarter perspective view of a blunt needle tip.

In another embodiment, the distal end of insert 34 in FIG. 7 or two-part crimped needle 10 is provided with a blunt tip configuration as shown in FIGS. 8a-8c. There is no sharp tip or puncture edge, but the tip 52 may be imparted with a chamfer, fillet, radius, or other feature that allows it to pass smoothly through the lumen 48 of the dilator 42 (FIG. 6a). This transseptal puncture device 38 embodiment is intended to be used with a sharp tip guidewire 50 (not shown), or sharp tipped stylet 51 (not shown). The septum may be tented as is the conventional medical practice, by using the tip of the blunt dilator 42 and/or the tip 52 of the blunt needle 10. The sharp tip guidewire 50 is then used to puncture the septum. The sharp tip guidewire 50 and blunt needle 10 may then be advanced into the left atrium. This embodiment is advantageous because a sharp needle tip is not needed when utilizing a sharp tip guidewire 50. The blunt tip needle 10 provides columnar support to the guidewire 50 while reducing the chance of skiving the dilator 42 during insertion, and because it is far less sharp than conventional penetrating needle tips, it poses a reduced risk of puncturing the left atrial free wall.

Not only may the blunt tip 52 of FIGS. 8a-8c may be included in the two-part needle construction, but any other known needle tip configuration, may be used with the disclosed crimped two-part needle construction.

FIG. 10 is a side view of the distal portion of an embodiment of a transseptal puncture device 38 wherein the intermediate portion 56 of the needle 10 is designed with a predetermined flexibility. The proximal portion 58 of the needle 10 is rigid to provide column strength as it is passed through the introducer 32. The intermediate portion 56 of the needle 10 is manufactured or formed from a material such that it is more likely to bend than the proximal portion 58. For example, the immediate portion 56 may be composed of nitinol and annealed at 500 degrees Centigrade for 10 minutes to relieve stress in otherwise super-elastic nitinol wire in an as-drawn condition. Alternatively, the material may be made from a softer material than the proximal portion 58 or distal portion 60. For example, the intermediate portion 56 may be made of a polymer while the proximal portion 58 and distal portion 60 are made from a more rigid material, such as a steel, a nickel-titanium alloy, an elastomer, or a more rigid polymer. The intermediate portion 56 may alternatively be comprised of: a coil of more rigid material; a series of spaced bands; provided with slits, grooves, notches, dimples, or other surface or body modifications that thin portions of the wall of intermediate portion 56; or manufactured in a spiral configuration or with a spiral ribbon forming the wall or with a spiral thinning of the wall as shown in FIGS. 11a-11c such that the immediate portion 56 has the ability to flex.

The intermediate portion 56 may be welded to, crimped, attached by adhesives, or manufactured from the same piece or kind of material as the proximal portion 58 and distal portion 60. In one embodiment, the intermediate portion 56 is about 80 mm in length such that the desired or predetermined curve provided in the device 38 is fully defined by the intermediate portion 56.

The distal tip 16, 20, 52, or 54 is provided with an embodiment that allows directly or indirectly for easy puncturing through tough and/or fibrous septa. After passing through the septum, however, the ductile intermediate portion 56 is no longer supported by the introducer 32 and flexes. The flexing of the intermediate portion 56 moves the distal or puncturing tip 16, 20, 52, or 54 out of alignment with the proximal portion 58 of needle 10, thereby rendering it atraumatic to the anatomic structures directly aligned with the puncture location and initial puncturing direction.

FIG. 12 is a side view of the distal portion of an embodiment of a transseptal puncture device 38 similar to FIGS. 10, 11a-11c wherein the distal portion 60, not the intermediate portion 56, is manufactured or formed from a material or in such a manner that the distal portion 60 of device 38 is more likely to bend than the proximal portion 58.

FIG. 13 is a side view of the distal portion of an embodiment of a transseptal puncture device similar to FIG. 12, wherein the distal tip 60, not the intermediate portion 56, is manufactured or formed from a material such that it is more likely to bend than the proximal portion 58. Distal portion 60 may be formed with a predetermined curvature or bias so as to assume a J bend. This embodiment may be manufactured in a similar manner as a floppy guidewire with J-shape distal tip. When unsupported by the introducer 32, it assumes an atraumatic distal bend, thereby blocking the puncture edge from contacting other parts of the patient's anatomy.

Figure 14:
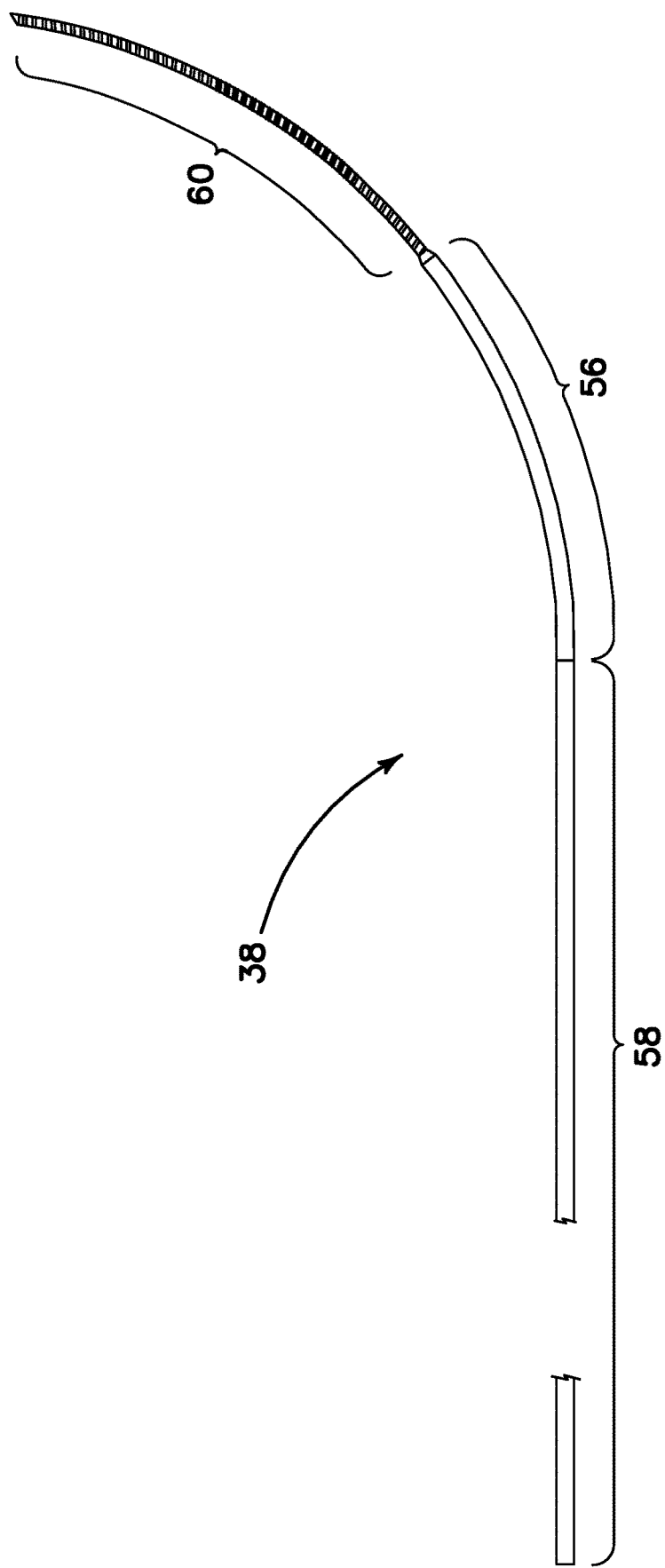
FIG. 14 is a side elevational view of the distal portion of an embodiment similar to the embodiment of FIG. 13 with the spiral tip substantially lengthened as compared to the J bend of FIG. 13.

FIG. 14 shows an embodiment similar to that shown in FIG. 13 with the modification that the spiral flexible tip portion 60 has been substantially lengthened according to requirements of the medical application in which device 38 is intended to be used.

FIG. 15a is a side elevational view of the distal portion of an embodiment of a transseptal puncture device 38 similar to FIG. 12, wherein the distal tip portion 60 and some intermediate portion 56 is manufactured or formed from a material such that it is more likely to bend than the proximal portion 58. The enlarged perspective view of FIG. 15b illustrates the spiral construction of distal portion 60 and intermediate portion 56 using a spirally wrapped ribbon 62, which is formed from a metal ribbon made of such as stainless steel or nitinol with a width of 0.2 to 0.8 mm and 0.1 to 0.25 mm thick with a helicity of 10 to 20 wraps per cm. Such a constructed distal portion 60 and intermediate portion 56 is readily flexible to any displacement perpendicular to the longitudinal axis of needle 10, but is substantially rigid to any longitudinal compression when needle 10 is confined within dilator 42 or introducer 32.

A stylet 64 may be used in conjunction with the transseptal puncture device 38. The stylet 64 locks onto the proximal hub 30 of the needle assembly 38 and is composed of metal, polymer, composite, rubber, ceramic, or glass, though preferably from a stainless steel or nickel titanium alloy.

The distal portion of the stylet 64 of FIG. 16 has an intermediate portion 56 some small predetermined distance, e.g. 1 to 10 mm, from the distal tip 16, 20 where intermediate portion 56 is manufactured in an manner or formed from a material that it is more likely to bend than the portions of the stylet 64 that are proximal or distal to the intermediate portion 56, similar to that described above. For example, the intermediate portion 56 may be necked down to a diameter of approximately 0.008" relative to the proximal portion 58 with a diameter of approximately 0.018" and distal portion 60 with a diameter of approximately 0.018" such that less force is required to flex in the intermediate portion 56. Alternatively, geometric, material, or structural modification may make the intermediate portion 56 more flexible, for example, by the introduction of slits, grooves, cut-aways, notches, dimples, flats, ovals, taper, or other modification that thins portions of the wall of the intermediate portion 56, which may or may not have a coating or extrusion of softer material covering the structural modification. The distal portion 60 or intermediate portion 56 may be made from a softer material such as shape memory alloy (SMA) that forms a curve when exposed to body temperatures. The intermediate portion 56 may also be comprised of a hinge or coil designed to easily and temporarily bend the stylet 64 off its longitudinal axis. The distal portion 60 may also be bent, curved, angled, or heat formed relative to the proximal portion 58 such that even less force is required to initiate the flex of the tip or the distal tip 16, 20 is less traumatic to body tissues than when it is straight. The end of the distal portion 60 may have a smooth, rounded, sphere, spherical, ball-end, or radiused tip to make the stylet even more atraumatic and prevent injury to cardiac tissue.

Figure 17A:
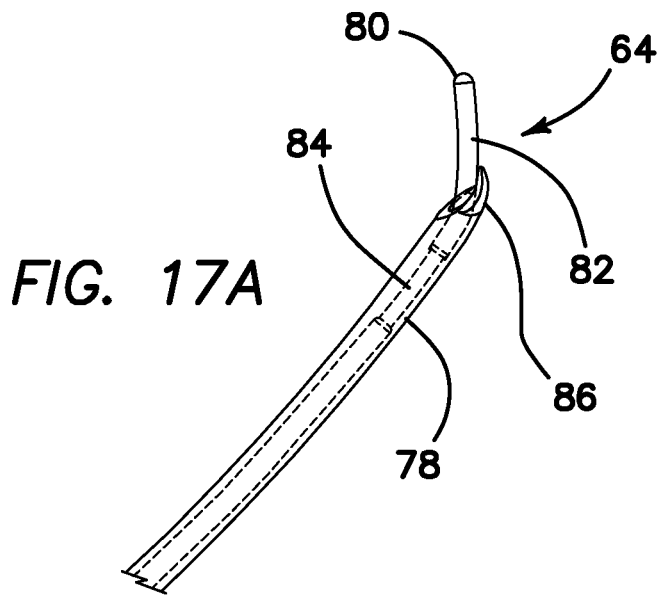
FIG. 17a is an enlarged view of distal end of the bird beak tipped needle and stylet of FIG. 17 with the stylet tip extending from the distal end of the blunt tipped needle, but with a reduced diameter portion of the stylet retained in the needle where its columnar strength is maintained.
Figure 17B:
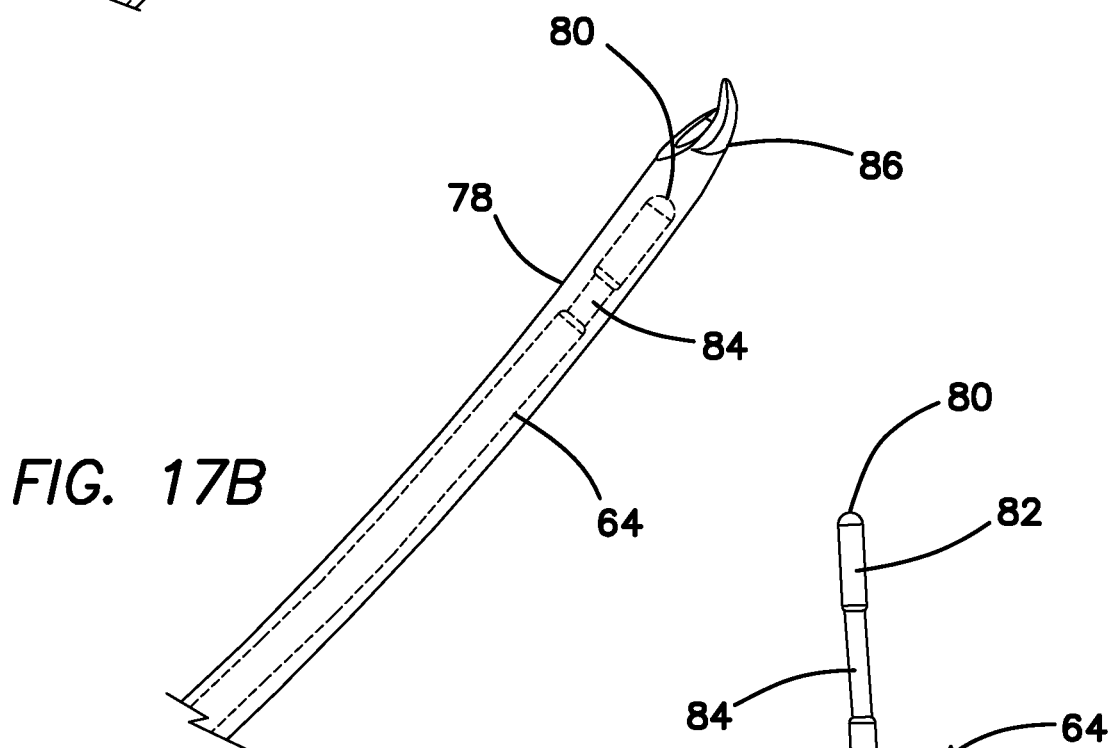
FIG. 17b is an enlarged view of distal end of the bird beak tipped needle and stylet of FIG. 17 with the stylet tip fully retracted within the needle.
Figure 25:
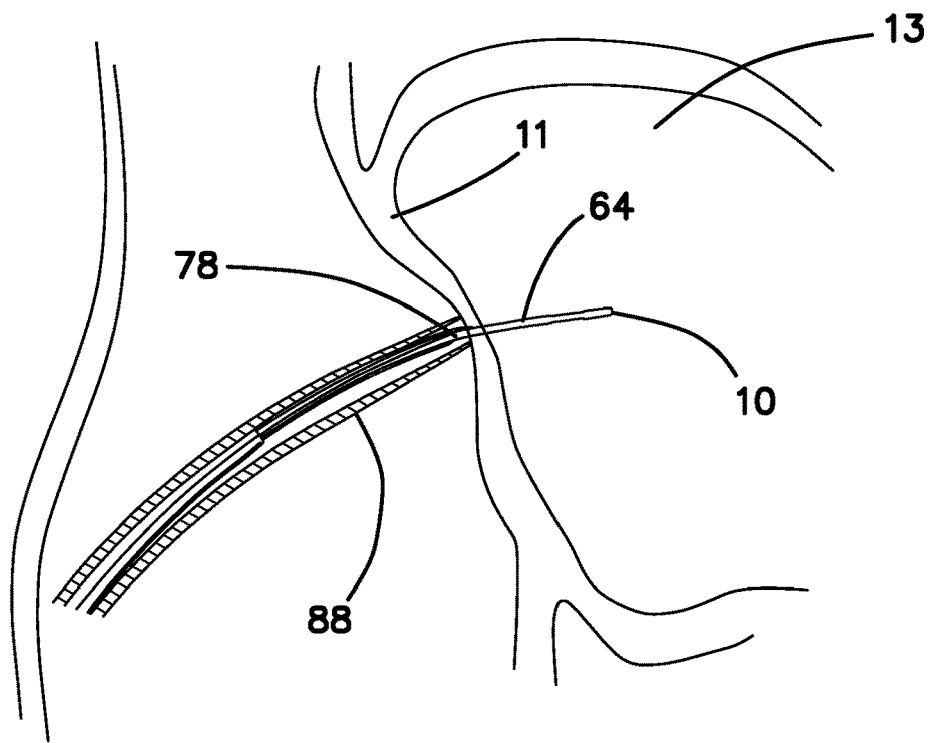
FIG. 25 is a diagrammatic cross sectional view of a heart in which an atrial transseptal procedure is being performed using a bird's beak tipped needle and stylet.

The operation of a stylet 64 and needle 78 is diagrammatically illustrated in FIG. 25. The operation of an atrial transseptal procedure can be seen to comprise four steps including: 1) a first step of tenting the septal wall 11 with a stylet 64 in a middle extension with respect to the needle 78 in which it is disposed as illustrated in FIG. 17a; 2) a second step in which the stylet 64 is pushed fully into the needle 78 as illustrated in FIG. 17b by the septum (11 FIG. 25); 3) a third step in which the needle 78 extends distally and penetrates septal wall 11 as illustrated in FIG. 25; and 4) a fourth step in which the stylet 64 springs forward through the needle 78 to protect the needle tip 86 from further penetration. FIG. 25 shows the curved introducer assembly 88 with bird's beak needle embodiment 10 pf FIG. 1b and stylet 64 in FIG. 17. The dilator 88 and stylet 64 are used to tent the septal wall 11. The sharp tip of the needle 78 then pierces the septal wall 11 once the stylet 64 has completely pushed into the needle 78, which allows the stylet 64 to spring forward into the left atrium 13 and assume an atraumatic configuration or shape. The dilator 88 is then able to advance over the needle 78 and stylet 64 into the left atrium 13.

Figure 26:
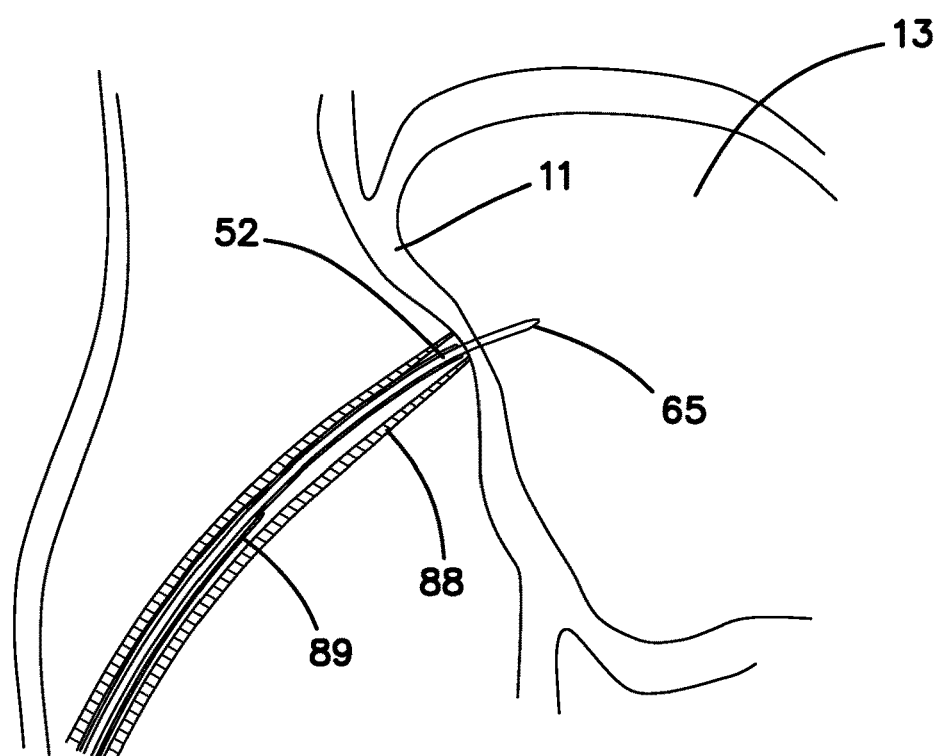
FIG. 26 is a diagrammatic cross sectional view of a heart in which an atrial transseptal procedure is being performed using a blunt tipped needle and sharp inner stylet.

FIG. 26 depicts a blunt tip needle 52 with sharp stylet 65. In this embodiment, the stylet 65 comprises a sharp tip that is used to puncture the septal wall 11. The blunt tip needle 52 is used only to provide columnar strength to the introducer assembly 88 and to aid in tenting the septal wall 11. Once the septal wall 11 is tented, the stylet 65 is advanced by the user, and the sharp tip punctures the septal wall 11. The stylet 65 then advances forward into the left atrium 13 and assumes an atraumatic configuration. The blunt tip needle 52 and dilator 88 may then be advanced over the stylet 65 into the left atrium 13.

A spring-like mechanism 66 is attached to the proximal end of the stylet 64 as shown in FIG. 16. The spring-like mechanism may take the form of one or a plurality of linear springs, torsional springs, gears, elastics, joints, pneumatics, buttons, or any other means of producing the desired reactive forces. Various embodiments of spring mechanism 66 are discussed below in connection with FIGS. 17-24. The proximal portion 58 or stylet wire feeds into the spring-like mechanism 66 while the locking portion 68 connects to the needle hub 30 (not shown). The spring-like mechanism 66 is formed from any spring or elastic material that acts in a way such that in its extended state it tends to return to its unextended or neutral length. The spring-like mechanism 66 is manufactured from a spring metal, polymer, elastomer, rubber, a nickel titanium alloy or superelastic material. It is comprised of one or a plurality of coils 92 and pistons 70.

One embodiment of spring mechanism 66 is shown in FIG. 18 wherein a housing 90, forming part of hub assembly 30, includes a compression spring 92 bearing against a piston 70, which is slidingly disposed into housing 90 and to which stylet 64 is attached.

In one embodiment shown in FIG. 19, the spring-like mechanism 66 and hub assembly 30 contains a slider 94 which is set into a slot 96 defined into housing 90 and coupled to the spring 92 and/or stylet 64. The slider 94 may move within the bounds of the slot 96 with the compression and extension of the spring 92 as the stylet 64 moves through the previously discussed motions, or the slider 94 may be manually compelled to move along the slot 96 by the user. At the proximal and distal ends of the slot 96 are locking structures (not shown) which provide a means to halt and temporarily hold the motion of the slider 94 at the extremes of its movement. For example, the slider and coupled stylet assembly may be compelled to move to the most distal end of the slot 96 and join with the locking structure, thereby temporarily fixing the slider's position.

When inserted into and locked onto the proximal hub 30 of the needle 10, the stylet tip 80 is useful to prevent skiving of the dilator 42 as the needle 10 is advanced by extending from the needle tip by a predetermined amount, e.g. 1 to 10 mm, and guiding the needle tip away from the inner wall of the dilator. When the needle 10 is positioned to tent the septum, the distal end of the stylet 64 is pushed back into the housing 90, thereby extending the spring-like mechanism 66 at the proximal end and exposing the needle tip 16, 20, enabling the needle tip 16, 20 to puncture the septum. When the needle 10 punctures the septum, the stylet 64 springs forward through the puncture hole, allowing the stylet tip 80 and intermediate portion 56 to protrude from the needle tip 16, 20 into the left atrium. Now unsupported by the needle 10, or dilator 42, the intermediate portion of the stylet 56 is able to flex, allowing the tip portion 82 to bend. This bent tip renders the stylet 64 atraumatic and ensures that if the needle assembly 38 were to continue forward to contact the atrial free wall, then the bend in the tip portion 82 of stylet 64 prevents the needle tip 16, 20 from puncturing the anatomy. Furthermore, the stylet proximal portion 58 may also extend past the needle tip 16, 20 to ensure that the needle tip 16, 20 is adequately shielded from further puncturing.

In one embodiment, the spring-like mechanism 66 and hub assembly 30 contains a lock or latch that clasps to the stylet lock 68. This ensures that the stylet tip 80 remains protruding from the needle tip until the lock or latch is released and maintains the atraumatic arrangement of the needle tip 16, 20 and stylet tip 80 while they reside in the left atrium of the heart. A mechanism such as a cam 74 used in a ball point pen allows the stylet 64 to lock and unlock.

FIG. 17a depicts a stylet 64 of assembly 30 of FIG. 17 in a middle position in relation to a needle 78. The stylet tip 80 extends the tip portion 82 of stylet 64 by a small amount, i.e. 1 to 4 mm, from the distal end 86 of the needle 78 to reduce skiving of the distal end 86 on the introducer assembly or dilator 88 (not shown in FIG. 17a). This stylet 64 comprises an intermediate portion 84, which has been necked down or ovalized for greater flexibility. As the intermediate portion 84 remains supported by the needle 78, the stylet 64 maintains its columnar strength.

FIG. 17b depicts the stylet 64 in the fully retracted position in relation to a needle 78. The stylet tip 80 does not extend at all from the distal end 86 of the needle 78. This may occur when the needle 78 is tenting the septum, and therefore the septum exerts opposing force to push the stylet tip 80 into the needle 78. Alternatively, the spring-like mechanism 66 may contain a feature wherein the user is able to pull back the stylet 64 so that it no longer protrudes from the needle tip 86.

Figure 17C:
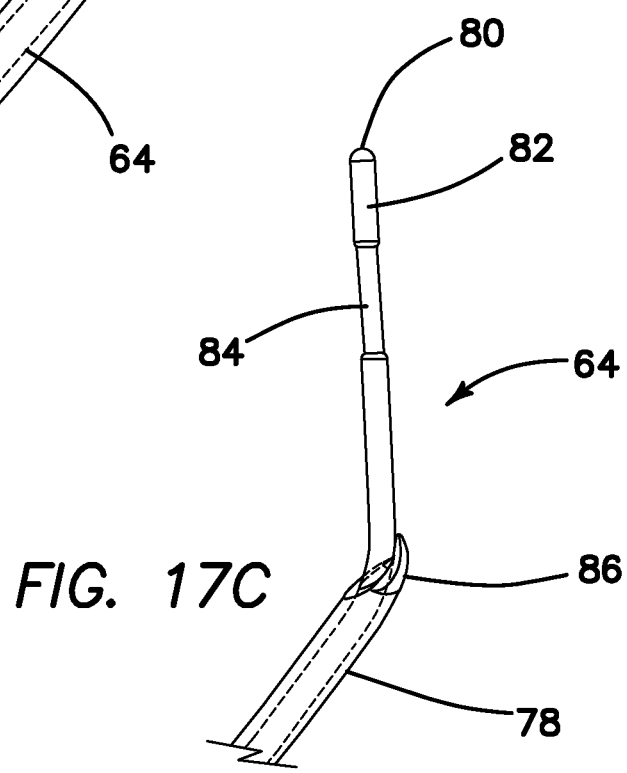
FIG. 17c is an enlarged view of distal end of the bird beak tipped needle and stylet of FIG. 17 with the stylet tip fully extended from the needle.

FIG. 17c depicts the stylet 64 in the fully extended position in relation to a needle 78. The stylet tip 80 extends out by a greater amount, i.e. 4 to 10 mm, from the needle tip 86. The intermediate portion 84 of the stylet 64 protrudes fully from the needle tip 86, allowing it to flex if necessary to prevent the needle tip 86 from contacting other anatomical structures.

In the embodiment shown in FIG. 20, the stylet 64 starts in the middle position of arcuate slot 100. Housing 90 includes a concentrically included inner slidable housing 91 to which stylet 64 is indirectly coupled. A pin 98 coupled to housing 90 rests in an arcuate slot 100 initially near the etched or printed "X" 104 on housing 91, which provides a visual representation that the stylet 64 is positioned in the middle, partially retracted configuration similar to FIG. 17a. During tenting of the septum, the stylet 64 is pushed back, retracting the pin 98 in arcuate slot 100 to a rearward position 106 and compressing the spring 70, which pushes the knob 102 away from the housing 90. As soon as the needle 78 (not shown in FIG. 20) punctures the septum, the spring 70 pushes the stylet 64 forward into its fully extended position similar to that shown in FIG. 17c. This motion also slides the knob 102 and pin 98 forward in arcuate slot 100 to the position shown in FIG. 20. The angled wall 108 prevents the pin 98 from returning to the "X" side 104 of the slot 100, so the pin 98 and stylet 64 continue to slide to the most distal end of the slot 100. An audible snap can be heard when the spring 70 pushes the knob 102, pin 98, and stylet 64 to the most distal position. The pin 98 positioned near the etched or printed "0" 110 provides a visual representation that the stylet 64 is now positioned in the fully extended position similar to that shown in FIG. 17c. To reset the stylet 64 and pin 98 assembly to the middle position, the user may pull the knob 102 away from the housing 90 to retract the stylet 64, rotate the knob 102 counter clockwise to push the pin 98 around the angled wall 108, and then release the knob 102 to allow the spring 70 to push the pin 98 into the "X" slot 104.

In another embodiment as shown in FIG. 21, the movement of stylet 64 is driven by an extension spring 70 and a full rotation slot 112, which means that slot 112 extends fully around inner housing 91 and is defined only partly into inner housing 91, which remains an integral or one-piece element. This allows knob 102 to be fully rotated by 360° returning in one turn to its initial position. In this embodiment spring 70 is extended between the inner and outer housings 90 and 91 to produce the spring mechanism 66 more proximately relative to the patient instead of more distally from the patient as in the embodiment of FIG. 20. The stylet 64 begins in the middle position divot 114. At this point, a pin 118, which is connected to housing 90 and engages with a rotating cylindrical housing 91 and knob 102, sits in a divot 114 of the arcuate slot 112. When the stylet 64 is pushed back during tenting, the spring 70 begins to extend, pushing and rotating the cylindrical housing 91 to the most proximal position 120 in the slot 112. This is the fully retracted position. When the needle punctures the septum, the extension spring 70 forcefully compresses, thereby extending and sending the stylet 64 forward to protrude fully from the tip of the needle (not shown). During this action, the cylindrical housing 91 moves distally until pin 118 hits the most distal end 122 of the slot 112 with an audible click. This noise serves as an auditory, visual, and tactile signal that the stylet 64 has reached its maximal extension distance. The knob 102 may then be rotated clockwise in relation to the cylindrical housing 90 such that the coupled pin 118 follows the slot 112 back down into the divot 114. This movement partially extends the spring 70 and retracts the stylet 64 back to the middle position.

Figure 22:
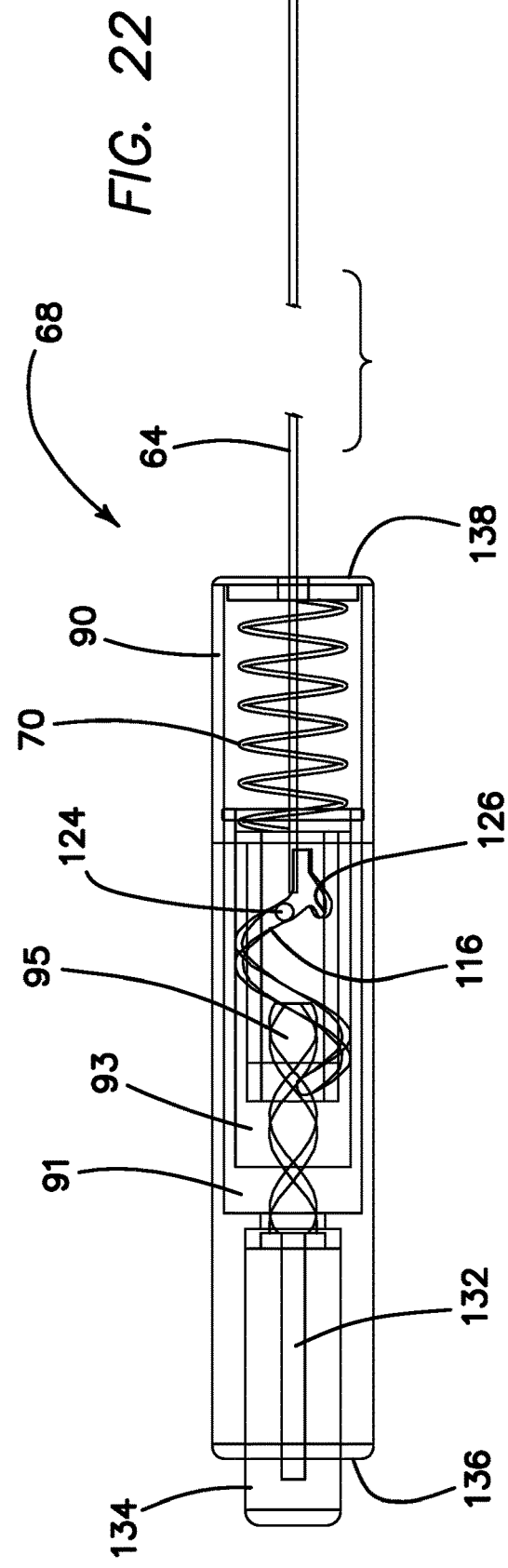
FIG. 22 is a side plan view of still yet another embodiment of the hub assembly and spring mechanism coupled to a stylet.

In another embodiment shown in FIG. 22, the movement is driven by a compression spring 70 and a partial rotation or arcuate slot 116. The stylet 64 begins in the middle position 126. At this point, a pin 124, which is connected to housing 91, sits in a notch 126 of the arcuate slot 116. Housing 90 includes a concentric inner slidable housing 91, an intermediate concentric housing 93 in which slot 116 is defined and bearing against spring 70. Pin 124 is fixed to inner housing 91 and is disposed in slot 116. When the stylet 64 is pushed back during tenting of the septal wall, the spring 70 begins to extend, which causes the cylinder 91 fixed to the pin 124 to rotate. The pin 124 slides down to the most proximal end 130 of the slot 116 extending spring 70. When the needle (not shown) punctures the septum, the spring 70 forcefully compresses, thereby moving the stylet 64 into its fully extended position similar to FIG. 17c. This motion pulls housing 93 down with the spring 70 along with pin 124 in arcuate slot 116, which causes the cylinder 91 to rotate. The rotating cylinder 91 slides with pin 124 along the length of arcuate slot 116. This rotational motion also causes the screw 95 rotationally fixed to housing 90 and which is coupled to a button 134 that protrudes from the distal end 136 of the housing 90 to move linearly due to keyway 132. Screw 95 is freely threaded into housing 91, and the coupled button 134 is keyed to housing 90 so that it may slide in and out of housing 90, but may not rotate therein. It is also within the scope of the invention that rotation of button 134 on screw 95 is free so that frictional restraint of button 134 by its manual depression substantially prevents its rotation and thus causes screw 95 to rotate as button 134 is depressed. The rotational motion of the screw 95 causes a linear motion that drives the button 134 to protrude farther from the housing 90. To retract the spring 70, the user may compress the button 134. The button 134 is coupled to the screw 95, which is driven forward and causes the cylinder 91 to rotate. The cylinder rotation drives the pin 124 around the slot 116 towards the proximal end 138 of housing 90. The pin motion causes the slot 116 to move distally, which extends the spring 70. The motion stops when the pin 124 reaches the notch 126, and the stylet 64 is therefore placed back in its middle position similar to that shown in FIG. 17a.

Figure 23:
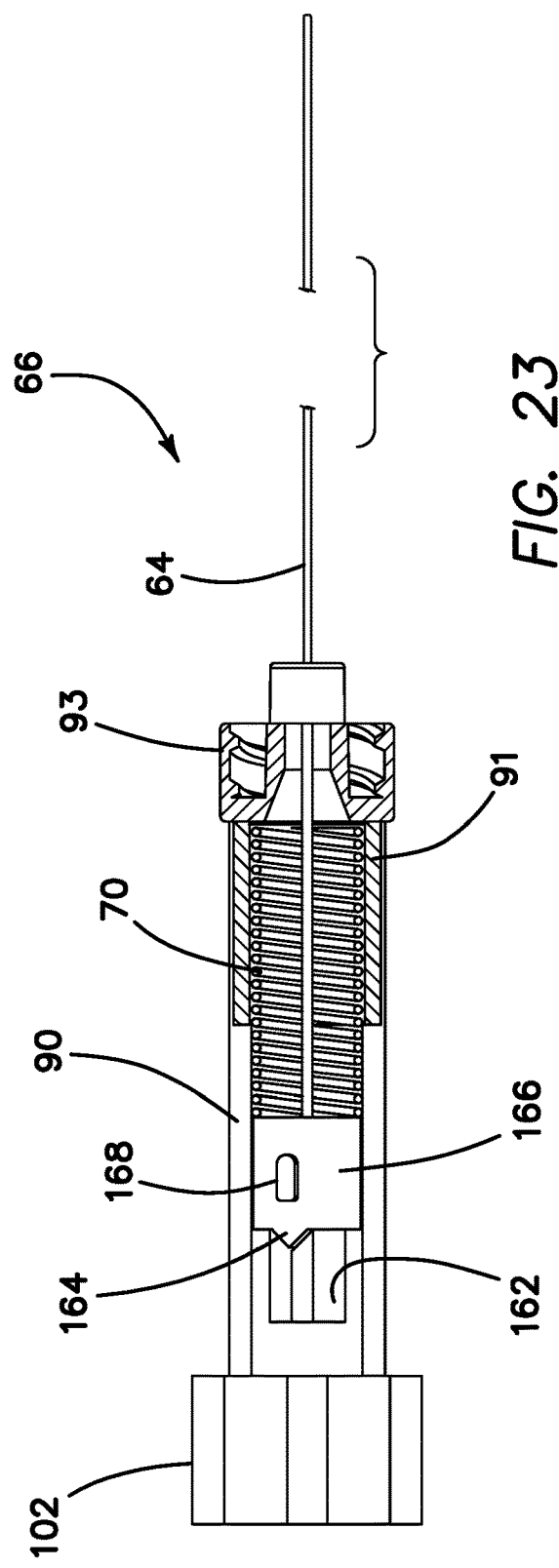
FIG. 23 is a side plan view of another embodiment of the hub assembly and spring mechanism coupled to a stylet.

In the embodiment of FIG. 23 an angled tooth cam 162 rotates with the knob 102. Outer housing 90 has a threaded end proximal to the patient. Inner housing 91 slidingly disposed within outer housing 90 has an end cap 93 threadably coupled to the proximal threaded end of outer housing 90. End cap 93 is rotatable with outer housing 90 by means of manual rotation of knob 102. Spring 70 is captively retained within outer and inner housings 90 and 91, which are coupled together, and bears against end cap 93. Spring 70 is coupled at one end to housing 91 and at its opposing end to slider 166. The user holds the outer housing 90 and/or knob 102 and pushes and rotates pusher 168 with an arcuate slot (not shown) defined in outer housing 90 so that cam tooth 164 is rotated relative to cam body 162 and stylet 64 extended or withdrawn according to control of the cammed surfaces. As the cam body 162 rotates tooth 164 rides up on the cammed surface and pushes slider 166 and stylet 64 to which slider 166 is connected toward the patient. The cam body 162 may be provided with a plurality of cam surfaces on which cam tooth 164 rides so that the relative positions described in connection with FIGS. 17a-17c can be configured. In the fully retracted position shown in FIG. 23, stylet 64 is retracted within needle 78. When cam tooth 164 rides up onto the cam surface of cam body 162, the septum will be tented and penetration of the septal wall follows. Rotation of tooth 164 onto the cam surface when cam body 162 is rotated with knob 102 ensures that the stylet tip 72 remains in its extended state until the lock or latch 168 is released. This maintains the atraumatic configuration of the needle tip 16, 20 and stylet tip 72 while in the left atrium of the heart. Extension spring 70 extends when stylet 64 is pushed back into housing 90 in the fully retracted position. Relative rotation of knob 102 with respect to pusher 168 thus controls the degree of compression of spring 70.

Figure 24:
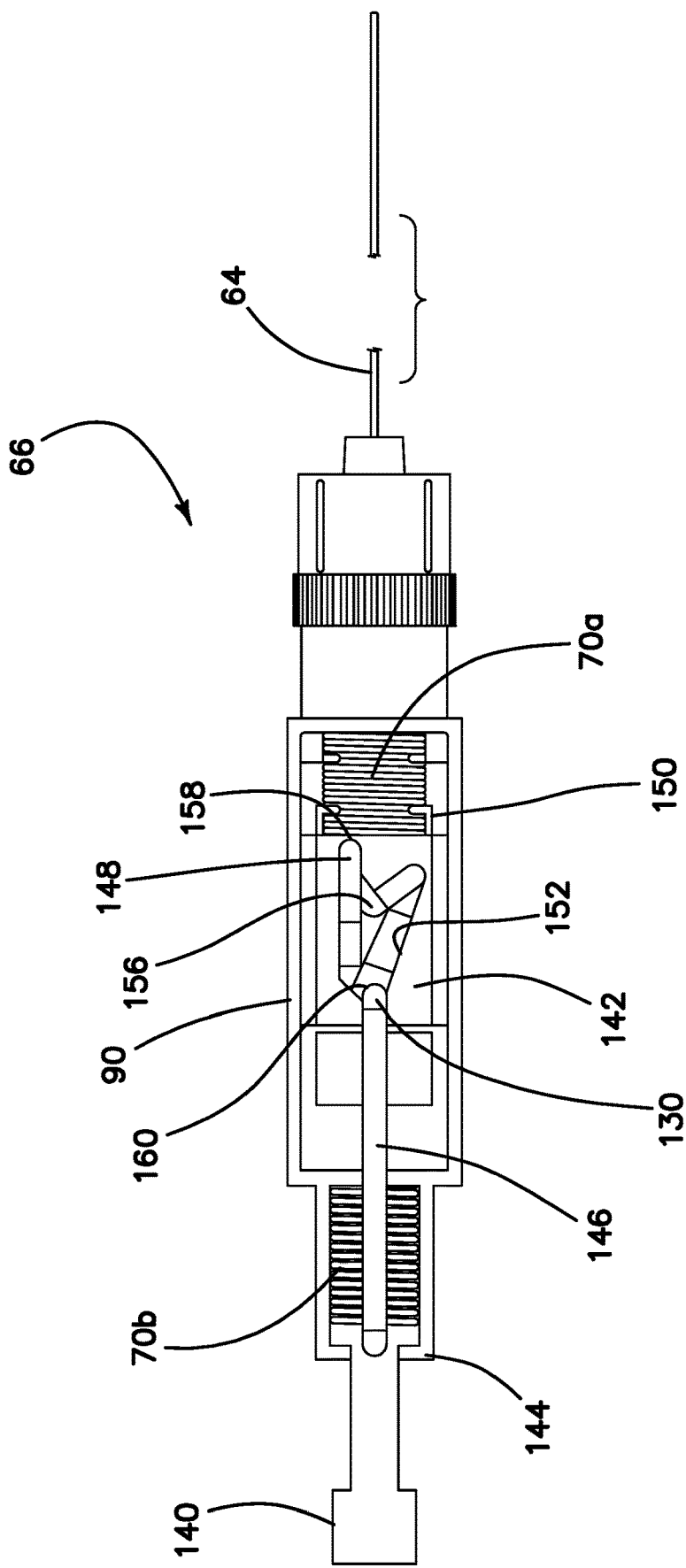
FIG. 24 is a side plan view of yet another embodiment of the hub assembly and spring mechanism coupled to a stylet.

In another embodiment shown in FIG. 24, the movement is driven by two springs, an extension spring 70a, a compression spring 70b and a hinged pin 130. The button 140 is coupled to compression spring 70b and a hinged pin 130 which is rotatable about pivot 144. The pin 130 is pivoted where it is coupled to the button 140, while an arm 146 extends the distal end pin 130 for coupling with the complexly shaped slot 148 defined in a slider 142, which is slidable (and alternatively rotatable as in FIG. 22) within housing 90. Arm 146 is axially positioned within housing 90, but longitudinally slidable therein. The proximal end 150 of the slider 142 relative to the patient is coupled to the stylet 64 and extension spring 70a. Distal movement of slider 142 relative to the patient thus draws stylet 64 back or away from the patient. Proximal movement of slider 142 relative to the patient pushes stylet 64 toward the patient. In an embodiment where slider 142 has a square cross section shape at least one position and slides in a corresponding rectangular cavity defined by housing 90, pin 130 pivots or rotates as it rides in slot 148 on a face of slider 142. In another embodiment slider 142 is cylindrical with a round or circular cross section in a corresponding cylindrical cavity defined by housing 90, slider 142 and stylet 64 rotate as slider 142 moves toward or away from the patient out.

Prior to beginning the motion, the stylet 64 rests in its most proximal position relative to the patient while the pin 130 is positioned in slot 148 at its most distal position 160. In this position, the introducer assembly (not shown) is able to be inserted into the patient and tent the septum. When the septum is tented, the stylet 64 is pushed back by the septum into the needle (not shown) similar to that shown in FIG. 17b. This movement extends the extension spring 70a and moves the slider 142 distally from the patient, which causes the pin 130 to move into the most proximal point 158 of the slot 148. Once the needle 78 punctures the septum, the extension spring 70a compresses forcefully, which causes the stylet 64 to spring proximally toward the patient and into the left atrium. Slider 142 moves proximally toward the patient in the housing 90, which is handheld in a fixed location. This movement causes the slider 142 to move relative to the pin 130 such that the pin 130 is now positioned at the intermediate portion 156 of the slot 148, compression spring 70b is partially extended and button 140 is still fully extended out of housing 90. To return the slider 142 to its original position, the button 140 is pressed into housing 90, the compression spring 70b shortens or compresses. This movement causes the pin 130 to move down the angled portion 152 of the slot 148. When the fully depressed button 140 is released by the user, the compression spring 70b expands and overcomes the force of extension spring 70a. As the pin 130 can only move along the path of the slot 148 and along the edge 154, the pin 130 returns to the original position. The spring mechanism 66 is now fully returned to its original position, and the transseptal procedure may be reperformed with a subsequent button press.

Additional embodiments of the above mechanisms have also been conceived that facilitate the stylet 64 locking in an intermediate position so that once the septum 11 (not shown) has been punctured by the needle, the stylet advances beyond the needle tip and locks in place, only to be re-set by pushing a button or rotating a knob on the proximal portion of the device (from the user perspective). This locking mechanism allows the stylet to have a more rigid distal portion or a lighter spring within the mechanism as the locking will prevent the stylet from inadvertently pushed back into the needle and subsequently exposing the sharp needle tip. These embodiments also have the ability for the stylet 64 to have an initial shorter projection from the needle tip when tenting the septum, and a longer projection from the needle tip once the septum has been crossed by the needle.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A hollow needle assembly for a transseptal cardiac needle comprising:
   a distal portion;
   a proximal portion; and
   a spring mechanism coupled to the hollow needle assembly such that the spring mechanism is loaded when the hollow needle assembly is advanced against a predetermined position on a septal wall, and where the spring mechanism is unloaded after the transseptal cardiac needle penetrates the septal wall allowing the distal portion of the transseptal cardiac needle to extend unsupported and thereby assume an atraumatic configuration, where the distal portion of the transseptal cardiac needle is comprised of material that is more flexible relative to the proximal portion.

2. The hollow needle assembly for a transseptal cardiac needle of claim 1 where the distal portion of the transseptal cardiac needle comprises a spiral structure providing it with increased flexibility as compared to the proximal portion.

3. The hollow needle assembly for a transseptal cardiac needle of claim 2 where the distal portion of the transseptal cardiac needle includes a defining wall and where the spiral structure comprises thinning the defining wall of the distal portion in a spiral pattern.

4. The hollow needle assembly for a transseptal cardiac needle of claim 2 where the distal portion of the transseptal cardiac needle is comprised of a spiral wrap.

5. The hollow needle assembly for a transseptal cardiac needle of claim 4 where the distal portion of the transseptal cardiac needle has a predetermined curve defined therein.

6. The hollow needle assembly for a transseptal cardiac needle of claim 1 where the distal portion of the transseptal cardiac needle includes a defining wall and where the structure comprises thinning the defining wall of the distal portion.

7. The hollow needle assembly for a transseptal cardiac needle of claim 1 where the distal portion of the transseptal cardiac needle comprises an inherently flexible material.

8. The hollow needle assembly for a transseptal cardiac needle of claim 7 where the inherently flexible material is nitinol.

9. The hollow needle assembly for a transseptal cardiac needle of claim 1 further comprising a stylet coupled to the spring mechanism such that the spring mechanism is loaded when the stylet is advanced against a predetermined position on a septal wall, and where the spring mechanism is unloaded after the transseptal cardiac needle penetrates the septal wall allowing the distal portion of the transseptal cardiac needle to extend unsupported and thereby assume an atraumatic configuration.

10. The hollow needle assembly for a transseptal cardiac needle of claim 1 where the transseptal cardiac needle comprises a bird beak tip, the bird beak tip comprising:
an inner surface; and
an outer surface, where the bird beak tip has a longitudinal axis and a leading edge of the bird beak tip, where the leading edge of the bird beak tip is located at and adjacent to the distal end of the inner and outer surfaces, where the inner surface of the hollow transseptal cardiac needle defines an opening of the bird beak tip, and where the distal end of the bird beak tip is curved relative to the longitudinal axis of the hollow transseptal cardiac needle into the opening of the bird beak tip.

11. The hollow needle assembly for a transseptal cardiac needle of claim 9 where the stylet comprises:
a distal portion; and
a proximal portion,
where the distal portion is comprised of material that is more flexible relative to the proximal portion.

12. The hollow needle assembly for a transseptal cardiac needle of claim 1 where the transseptal cardiac needle comprises a tip, the tip comprising:
an inner surface of the needle;
an outer surface of the needle, where the inner and outer surfaces of the needle have a common longitudinal axis;
a bevel provided on a distal end of the needle to define a face of the needle; and
a pair of opposing side bevels defined into a distal end of the face of the needle, the side bevels intersecting at the distal end of the needle to define the needle tip,
where the distal end of the needle and the needle tip bends toward the longitudinal axis of the needle.

13. A method of using a spring mechanism coupled to an elongate stylet or needle for a transseptal cardiac procedure comprising:
providing a stylet or needle comprising a distal portion and a proximal portion, where the distal portion is flexible relative to the proximal portion;
disposing the stylet or needle into an atrium in a heart oriented toward a selected position against a septal wall, the stylet or needle being coupled to the spring mechanism;
advancing the stylet or needle against the selected position on the septal wall while tenting the septal wall and while spring loading the spring mechanism; and
automatically unloading the spring mechanism as the stylet or needle penetrates the septal wall allowing the stylet or needle to extend unsupported into an opposing atrium and to assume an atraumatic configuration.

14. The method of claim 13 where providing the stylet or needle comprising a distal portion and a proximal portion comprises providing the distal portion with a spiral structure.

15. The method of claim 14 where providing the distal portion with a spiral structure comprises thinning a defining wall of the distal portion in a spiral pattern.

16. The method of claim 13 where providing the stylet or needle comprising a distal portion and a proximal portion comprises providing the distal portion with a spiral wrap.

17. The method of claim 13 where providing the stylet or needle comprising a distal portion and a proximal portion comprises providing a distal portion that is comprised of an inherently flexible material.

18. The method of claim 17 where providing a distal portion that is comprised of an inherently flexible material comprises a distal portion that is comprised of nitinol.

19. The method of claim 13 further comprising locking the spring mechanism so that the stylet is fixed in position relative to the needle and serves to atraumatically prevent advancement of the needle into heart tissue.

20. The method of claim 13 further comprising emitting a visual, audible, or tactile response from the spring mechanism to indicate when the stylet or needle is tenting the septal wall and/or when the needle has perforated the septal wall.

* * * * *